United States Patent [19]
Chan et al.

[11] Patent Number: 5,834,587
[45] Date of Patent: Nov. 10, 1998

[54] G-PROTEIN COUPLED RECEPTOR, HLTEX 11

[75] Inventors: Winnie Chan, West Chester; Derk J. Bergsma, Berwyn, both of Pa.; Catherine E. Ellis, Glassboro, N.J.

[73] Assignee: SmithKline Beecham Corporation, Philadelphia, Pa.

[21] Appl. No.: 726,575

[22] Filed: Oct. 8, 1996

[51] Int. Cl.⁶ .................................................. C07K 14/705
[52] U.S. Cl. .......................... 530/324; 530/325; 530/326; 530/350; 514/2
[58] Field of Search .................................... 530/350, 300, 530/324–326; 514/2

[56] References Cited

PUBLICATIONS

Nakamura, M., et al., Molecular Cloning and Expression of Platelet–Activating Factor Receptor from Human Leukocytes, *J. Biol. Chem.*, 1991, 266(30):20400–20405.

Kaplan, M.H. et al., Identification of a G Protein Coupled Receptor Induced in Activated T Cells, *J. Immun.*, 1993, 151:628–636.

McKernan et al. Heterogeneity Between Soluble Human and Rabbit Splenic alpha2–Adrenoceptors. Biochemical Pharmacology 35(20):3517–3523, Oct. 15, 1986.

*Primary Examiner*—John Ulm
*Attorney, Agent, or Firm*—Paul F. Prestia; William T. Han; William T. King

[57] ABSTRACT

Human HLTEX11 polypeptides and DNA (RNA) encoding such HLTEX11 and a procedure for producing such polypeptides by recombinant techniques is disclosed. Also disclosed are methods for utilizing such HLTEX11 for the treatment of atherosclerosis, inflammatory conditions, and infections, particularly viral infections, such as AIDS, among others, among others, are also disclosed. Also disclosed are diagnostic assays for detecting diseases related to mutations in the nucleic acid sequences and altered concentrations of the polypeptides. Also disclosed are diagnostic assays for detecting mutations in the polynucleotides encoding the HLTEX11 and for detecting altered levels of the polypeptide in a host.

5 Claims, 2 Drawing Sheets

| | | | | |
|---|---|---|---|---|
| 1 | AGGTACGCCT | GCAGGTACCG | GTCCGGAATT | CCCGGGTCGA |
| 41 | CCCACGCGTC | CGGTTATCAG | CAGGATCCAT | GCCGCCAGAG |
| 81 | TAAAGCTTTC | TACCCTTTAC | TCCCTGCAAA | GAAACAAGAG |
| 121 | TGCTTATCCC | AGCTAAGCTC | CAGGGTTAAA | ACTCTATGCT |
| 161 | GGTCATTCCC | TTCAGGATTT | GGCACTCACC | AACATACCCT |
| 201 | TCTTTCAAGT | GAAAAGGCAT | CTCTTTTAAT | GGTCCTGACC |
| 241 | TTTGGAATAG | GAAGCATGTA | CCCTGGACAG | AGCACTTCAA |
| 281 | ACTAGAGGAA | CCATAAATCC | ATGGCTAACC | TTGACAAATA |
| 321 | CACTGAAACA | TTCAAGATGG | GTAGCAACAG | TACCAGCACT |
| 361 | GCTGAGATTT | ACTGTAATGT | CACTAATGTG | AAATTTCAAT |
| 401 | ACTCCCTCTA | TGCAACCACC | TATATCCTCA | TATTCATTCC |
| 441 | TGGTCTTCTG | GCTAACAGTG | CAGCCTTGTG | GGTTCTGTGC |
| 481 | CGCTTCATCA | GCaAGaaaaa | TAAAGCCATC | ATTTTCATGA |
| 521 | TCAACCTCTC | TGTGGCTGAC | CTTGCTCATG | TATTATCTTT |
| 561 | ACCCCTCCgG | ATTTACTATT | ACATCAGCCA | CCACTGGCCT |
| 601 | TTCCAGAGAG | CCCTTTGCCT | GCTCTGCTTC | TACCTGAAGT |
| 641 | ATCTCAACAT | GTATGCCAGC | ATTTGTTTCC | TGACGTGCAT |
| 681 | CAGTCTTCAA | AGGTGCTTTT | TTCTCCTCAA | GCCCTTCAGG |
| 721 | GCCAGAGACT | GGAAGCGTAG | GTACGATGTG | GGCATCAGTG |
| 761 | CTGCCATCTG | GATCGTTGTG | GGGACTGCCT | GTTTGCCATT |
| 801 | TCCCATCCTG | AGAAGCACAG | ACTTAAACAA | CAACAAGTCC |
| 841 | TGCTTTGCTG | ATCTTGGATA | CAAGCAAATG | AATGCAGTTG |
| 881 | CGTTGGTCGG | GATGATTACA | GTTGCTGAgC | TTGCAGGATT |
| 921 | TGTGATCCCA | GTGATCATCA | TCGCATGGTG | TACCTGGAAA |
| 961 | ACTACTATAT | CCTTGAgAcA | gCCACCAATG | GCTTTCCAAG |
| 1001 | GGATCAgTGA | gAGGCAGAAA | GCACTGCGGA | TGGTGTTCAT |
| 1041 | GTGTGCTGCA | GTCTTCTTCA | TCTGCTTCAC | TCCCTATCAT |
| 1081 | ATTAACTTTA | TTTTTTACAC | CATGGTAAAG | GAAACCATCA |
| 1121 | TTAGCAGTTG | TCCCGTTGTC | CGAATCGCAC | TGTATTTCCA |
| 1161 | CCCTTTTTGC | CTGTGCCTTG | CAAGTCTCTG | CTGCCTTTTG |
| 1201 | GATCCAATTC | TTTATTACTT | TATGGCTTCA | GAGTTTCGTG |
| 1241 | ACCAACTATC | CCGCCATGGC | AGTTCTGTGA | CCCGCTCCCG |
| 1281 | CCTCATGAGC | AAGGAGAGTG | GTTCATCAAT | GATTGGCTAA |
| 1321 | AATTAAGATA | TCTCTTTAAT | TACGCCTTTG | TTTACCTACG |
| 1361 | TTCCTTGTCT | TTTTCCAAAG | GCCAGAATTG | TCAACCAATT |
| 1401 | TCTTTAATTG | AACATTGTAA | AAAACAGGAA | TAAGTACTTT |
| 1441 | TGTgTAATAT | TCACAGTCAA | CAGGGgTGTG | ATGGTGAAGG |
| 1481 | CAGAgTgTGA | AAAACGTgaG | AGAggAAGAg | AaAAtAgATT |
| 1521 | TaCCTGAtT | | | |

FIG. 1A

```
1    RNHKSMANLD  KYTETFKMGS  NSTSTAEIYC  NVTNVKFQYS  LYATTYILIF
51   IPGLLANSAA  LWVLCRFISK  KNKAIIFMIN  LSVADLAHVL  SLPLRIYYYI
101  SHHWPFQRAL  CLLCFYLKYL  NMYASICFLT  CISLQRCFFL  LKPFRARDWK
151  RRYDVGISAA  IWIVVGTACL  PFPILRSTDL  NNNKSCFADL  GYKQMNAVAL
201  VGMITVAELA  GFVIPVIIIA  WCTWKTTISL  RQPPMAFQGI  SERQKALRMV
251  FMCAAVFFIC  FTPYHINFIF  YTMVKETIIS  SCPVVRIALY  FHPFCLCLAS
301  LCCLLDPILY  YFMASEFRDQ  LSRHGSSVTR  SRLMSKESGS  SMIG*
```

FIG. 1B

SEQUENCE LISTING ( 1 ) GENERAL INFORMATION:

( i i i ) NUMBER OF SEQUENCES: 5

( 2 ) INFORMATION FOR SEQ ID NO:1:

( i ) SEQUENCE CHARACTERISTICS:
        ( A ) LENGTH: 1529
        ( B ) TYPE: Nucleic Acid
        ( C ) STRANDEDNESS: Single
        ( D ) TOPOLOGY: Linear ( i v ) ANTI-SENSE: No ( x i ) SEQUENCE DESCRIPTION: SEQ ID NO: 1:

```
AGGTACGCCT  GCAGGTACCG  GTCCGGAATT  CCCGGGTCGA  CCCACGCGTC         50
CGGTTATCAG  CAGGATCCAT  GCCGCCAGAG  TAAAGCTTTC  TACCCTTTAC        100
TCCCTGCAAA  GAAACAAGAG  TGCTTATCCC  AGCTAAGCTC  CAGGGTAAA         150
ACTCTATGCT  GGTCATTCCC  TTCAGGATTT  GGCACTCACC  AACATACCCT        200
TCTTTCAAGT  GAAAAGGCAT  CTCTTTTAAT  GGTCCTGACC  TTTGGAATAG        250
GAAGCATGTA  CCCTGGACAG  AGCACTTCAA  ACTAGAGGAA  CCATAAATCC        300
ATGGCTAACC  TTGACAAATA  CACTGAAACA  TTCAAGATGG  GTAGCAACAG        350
TACCAGCACT  GCTGAGATTT  ACTGTAATGT  CACTAATGTG  AAATTTCAAT        400
ACTCCCTCTA  TGCAACCACC  TATATCCTCA  TATTCATTCC  TGGTCTTCTG        450
GCTAACAGTG  CAGCCTTGTG  GGTTCTGTGC  CGCTTCATCA  GCAAGAAAAA        500
TAAAGCCATC  ATTTTCATGA  TCAACCTCTC  TGTGGCTGAC  CTTGCTCATG        550
TATTATCTTT  ACCCCTCCGG  ATTTACTATT  ACATCAGCCA  CCACTGGCCT        600
TTCCAGAGAG  CCCTTTGCCT  GCTCTGCTTC  TACCTGAAGT  ATCTCAACAT        650
GTATGCCAGC  ATTTGTTTCC  TGACGTGCAT  CAGTCTTCAA  AGGTGCTTTT        700
TTCTCCTCAA  GCCCTTCAGG  GCCAGAGACT  GGAAGCGTAG  GTACGATGTG        750
GGCATCAGTG  CTGCCATCTG  GATCGTTGTG  GGGACTGCCT  GTTTGCCATT        800
TCCCATCCTG  AGAAGCACAG  ACTTAAACAA  CAACAAGTCC  TGCTTTGCTG        850
ATCTTGGATA  CAAGCAAATG  AATGCAGTTG  CGTTGGTCGG  GATGATTACA        900
GTTGCTGAGC  TTGCAGGATT  TGTGATCCCA  GTGATCATCA  TCGCATGGTG        950
TACCTGGAAA  ACTACTATAT  CCTTGAGACA  GCCACCAATG  GCTTTCCAAG       1000
GGATCAGTGA  GAGGCAGAAA  GCACTGCGGA  TGGTGTTCAT  GTGTGCTGCA       1050
GTCTTCTTCA  TCTGCTTCAC  TCCCTATCAT  ATTAACTTTA  TTTTTACAC        1100
CATGGTAAAG  GAAACCATCA  TTAGCAGTTG  TCCCGTTGTC  CGAATCGCAC       1150
```

-continued

```
TGTATTTCCA  CCCTTTTTGC  CTGTGCCTTG  CAAGTCTCTG  CTGCCTTTTG              1200

GATCCAATTC  TTTATTACTT  TATGGCTTCA  GAGTTTCGTG  ACCAACTATC              1250

CCGCCATGGC  AGTTCTGTGA  CCCGCTCCCG  CCTCATGAGC  AAGGAGAGTG              1300

GTTCATCAAT  GATTGGCTAA  AATTAAGATA  TCTCTTTAAT  TACGCCTTTG              1350

TTTACCTACG  TTCCTTGTCT  TTTTCCAAAG  GCCAGAATTG  TCAACCAATT              1400

TCTTTAATTG  AACATTGTAA  AAAACAGGAA  TAAGTACTTT  TGTGTAATAT              1450

TCACAGTCAA  CAGGGGTGTG  ATGGTGAAGG  CAGAGTGTGA  AAAACGTGAG              1500

AGAGGAAGAG  AAAATAGATT  TACCTGATT                                      1529
```

( 2 ) INFORMATION FOR SEQ ID NO:2:

( i ) SEQUENCE CHARACTERISTICS:
        ( A ) LENGTH: 344
        ( B ) TYPE: Amino Acid
        ( D ) TOPOLOGY: Linear ( x i ) SEQUENCE DESCRIPTION: SEQ ID NO: 2:

```
Arg  Asn  His  Lys  Ser  Met  Ala  Asn  Leu  Asp  Lys  Tyr  Thr  Glu  Thr
1              5                        10                       15

Phe  Lys  Met  Gly  Ser  Asn  Ser  Thr  Ser  Thr  Ala  Glu  Ile  Tyr  Cys
                    20                       25                       30

Asn  Val  Thr  Asn  Val  Lys  Phe  Gln  Tyr  Ser  Leu  Tyr  Ala  Thr  Thr
                    35                       40                       45

Tyr  Ile  Leu  Ile  Phe  Ile  Pro  Gly  Leu  Leu  Ala  Asn  Ser  Ala  Ala
                    50                       55                       60

Leu  Trp  Val  Leu  Cys  Arg  Phe  Ile  Ser  Lys  Lys  Asn  Lys  Ala  Ile
                    65                       70                       75

Ile  Phe  Met  Ile  Asn  Leu  Ser  Val  Ala  Asp  Leu  Ala  His  Val  Leu
                    80                       85                       90

Ser  Leu  Pro  Leu  Arg  Ile  Tyr  Tyr  Tyr  Ile  Ser  His  His  Trp  Pro
                    95                       100                      105

Phe  Gln  Arg  Ala  Leu  Cys  Leu  Leu  Cys  Phe  Tyr  Leu  Lys  Tyr  Leu
                    110                      115                      120

Asn  Met  Tyr  Ala  Ser  Ile  Cys  Phe  Leu  Thr  Cys  Ile  Ser  Leu  Gln
                    125                      130                      135

Arg  Cys  Phe  Phe  Leu  Leu  Lys  Pro  Phe  Arg  Ala  Arg  Asp  Trp  Lys
                    140                      145                      150

Arg  Arg  Tyr  Asp  Val  Gly  Ile  Ser  Ala  Ala  Ile  Trp  Ile  Val  Val
                    155                      160                      165

Gly  Thr  Ala  Cys  Leu  Pro  Phe  Pro  Ile  Leu  Arg  Ser  Thr  Asp  Leu
                    170                      175                      180

Asn  Asn  Asn  Lys  Ser  Cys  Phe  Ala  Asp  Leu  Gly  Tyr  Lys  Gln  Met
                    185                      190                      195

Asn  Ala  Val  Ala  Leu  Val  Gly  Met  Ile  Thr  Val  Ala  Glu  Leu  Ala
                    200                      205                      210

Gly  Phe  Val  Ile  Pro  Val  Ile  Ile  Ile  Ala  Trp  Cys  Thr  Trp  Lys
                    215                      220                      225

Thr  Thr  Ile  Ser  Leu  Arg  Gln  Pro  Pro  Met  Ala  Phe  Gln  Gly  Ile
                    230                      235                      240

Ser  Glu  Arg  Gln  Lys  Ala  Leu  Arg  Met  Val  Phe  Met  Cys  Ala  Ala
                    245                      250                      255

Val  Phe  Phe  Ile  Cys  Phe  Thr  Pro  Tyr  His  Ile  Asn  Phe  Ile  Phe
                    260                      265                      270
```

| | | | | | | | | | | | | | |
|---|---|---|---|---|---|---|---|---|---|---|---|---|---|
| Tyr | Thr | Met | Val | Lys<br>275 | Glu | Thr | Ile | Ile | Ser<br>280 | Ser | Cys | Pro | Val<br>285 |
| Arg | Ile | Ala | Leu | Tyr<br>290 | Phe | His | Pro | Phe | Cys<br>295 | Leu | Cys | Leu | Ala | Ser<br>300 |
| Leu | Cys | Cys | Leu | Leu<br>305 | Asp | Pro | Ile | Leu | Tyr<br>310 | Tyr | Phe | Met | Ala | Ser<br>315 |
| Glu | Phe | Arg | Asp | Gln<br>320 | Leu | Ser | Arg | His | Gly<br>325 | Ser | Ser | Val | Thr | Arg<br>330 |
| Ser | Arg | Leu | Met | Ser<br>335 | Lys | Glu | Ser | Gly | Ser<br>340 | Ser | Met | Ile | Gly |

( 2 ) INFORMATION FOR SEQ ID NO:3:

( i ) SEQUENCE CHARACTERISTICS:
        ( A ) LENGTH: 21
        ( B ) TYPE: Nucleic Acid
        ( C ) STRANDEDNESS: Single
        ( D ) TOPOLOGY: Linear ( i v ) ANTI-SENSE: No ( x i ) SEQUENCE DESCRIPTION: SEQ ID NO: 3:

GGATGGTGTT CATGTGTGCT G　　　　　　　　　　　　　　　　　　　　　　　　21

( 2 ) INFORMATION FOR SEQ ID NO:4:

( i ) SEQUENCE CHARACTERISTICS:
        ( A ) LENGTH: 20
        ( B ) TYPE: Nucleic Acid
        ( C ) STRANDEDNESS: Single
        ( D ) TOPOLOGY: Linear ( i v ) ANTI-SENSE: No ( x i ) SEQUENCE DESCRIPTION: SEQ ID NO: 4:

CTTCATCTGC TTCACTCCCT　　　　　　　　　　　　　　　　　　　　　　　　20

( 2 ) INFORMATION FOR SEQ ID NO:5:

( i ) SEQUENCE CHARACTERISTICS:
        ( A ) LENGTH: 20
        ( B ) TYPE: Nucleic Acid
        ( C ) STRANDEDNESS: Single
        ( D ) TOPOLOGY: Linear ( i v ) ANTI-SENSE: Yes ( x i ) SEQUENCE DESCRIPTION: SEQ ID NO: 5:

CACAGAACTG CCATGGCGGG　　　　　　　　　　　　　　　　　　　　　　　　20

G-PROTEIN COUPLED RECEPTOR, HLTEX 11

FIELD OF THE INVENTION

This invention relates, in part, to newly identified polynucleotides and polypeptides; variants and derivatives of the polynucleotides and polypeptides; processes for making the polynucleotides and the polypeptides, and their variants and derivatives; agonists and antagonists of the polypeptides; and uses of the polynucleotides, polypeptides, variants, derivatives, agonists and antagonists. In particular, in these and in other regards, the invention relates to polynucleotides and polypeptides of a G-protein coupled receptor, hereinafter referred to as "HLTEX 11".

BACKGROUND OF THE INVENTION

This invention relates to newly identified polynucleotides, polypeptides encoded by such polynucleotides, the use of such polynucleotides and polypeptides, as well as the production of such polynucleotides and polypeptides. More particularly, the polypeptides of the present invention are G-protein coupled receptors. The invention also relates to inhibiting or activating the action of such polypeptides.

It is well established that many medically significant biological processes are mediated by proteins participating in signal transduction pathways that involve G-proteins and/or second messengers, e.g., cAMP (Lefkowitz, *Nature*, 1991, 351:353–354). Herein these proteins are referred to as proteins participating in pathways with G-proteins or PPG proteins. Some examples of these proteins include the GPC receptors, such as those for adrenergic agents and dopamine (Kobilka, B. K., et al., *Proc. Natl Acad. Sci., USA*, 1987, 84:46–50; Kobilka, B. K., et al., *Science*, 1987, 238:650–656; Bunzow, J. R., et al., *Nature*, 1988, 336:783–787), G-proteins themselves, effector proteins, e.g., phospholipase C, adenyl cyclase, and phosphodiesterase, and actuator proteins, e.g., protein kinase A and protein kinase C (Simon, M. I., et al., *Science*, 1991, 252:802–8).

For example, in one form of signal transduction, the effect of hormone binding is activation of an enzyme, adenylate cyclase, inside the cell. Enzyme activation by hormones is dependent on the presence of the nucleotide GTP. GTP also influences hormone binding. A G-protein connects the hormone receptors to adenylate cyclase. G-protein has been shown to exchange GTP for bound GDP when activated by hormone receptors. The GTP-carrying form then binds to an activated adenylate cyclase. Hydrolysis of GTP to GDP, catalyzed by the G-protein itself, returns the G-protein to its basal, inactive form. Thus, the G-protein serves a dual role, as an intermediate that relays the signal from receptor to effector, and as a clock that controls the duration of the signal.

The membrane protein gene superfamily of G-protein coupled receptors has been characterized as having seven putative transmembrane domains. The domains are believed to represent transmembrane α-helices connected by extracellular or cytoplasmic loops. G-protein coupled receptors include a wide range of biologically active receptors, such as hormone, viral, growth factor and neuroreceptors.

G-protein coupled receptors have been characterized as including these seven conserved hydrophobic stretches of about 20 to 30 amino acids, connecting at least eight divergent hydrophilic loops. The G-protein family of coupled receptors includes dopamine receptors which bind to neuroleptic drugs used for treating psychotic and neurological disorders. Other examples of members of this family include calcitonin, adrenergic, endothelin, cAMP, adenosine, muscarinic, acetylcholine, serotonin, histamine, thrombin, kinin, follicle stimulating hormone, opsins, endothelial differentiation gene-1 receptor, rhodopsins, odorant, cytomegalovirus receptors, etc.

Most G-protein coupled receptors have single conserved cysteine residues in each of the first two extracellular loops which form disulfide bonds that are believed to stabilize functional protein structure. The 7 transmembrane regions are designated as TM1, TM2, TM3, TM4, TM5, TM6, and TM7. TM3 has been implicated in signal transduction.

Phosphorylation and lipidation (palmitylation or farnesylation) of cysteine residues can influence signal transduction of some G-protein coupled receptors. Most G-protein coupled receptors contain potential phosphorylation sites within the third cytoplasmic loop and/or the carboxy terminus. For several G-protein coupled receptors, such as the β-adrenoreceptor, phosphorylation by protein kinase A and/or specific receptor kinases mediates receptor desensitization.

For some receptors, the ligand binding sites of G-protein coupled receptors are believed to comprise a hydrophilic socket formed by the transmembrane domains of several G-protein coupled receptors, said socket being surrounded by hydrophobic residues of the G-protein coupled receptors. The hydrophilic side of each G-protein coupled receptor transmembrane helix is postulated to face inward and form the polar ligand binding site. TM3 has been implicated in several G-protein coupled receptors as having a ligand binding site, such as the TM3 aspartate residue. TM5 serines, a TM6 asparagine and TM6 or TM7 phenylalanines or tyrosines are also implicated in ligand binding.

G-protein coupled receptors can be intracellularly coupled by heterotrimeric G-proteins to various intracellular enzymes, ion channels and transporters (see e.g. Johnson et al., *Endoc., Rev.*, 1989, 10:317–331). Different G-protein cc-subunits preferentially stimulate particular effectors to modulate various biological functions in a cell. Phosphorylation of cytoplasmic residues of G-protein coupled receptors has been identified as an important mechanism for the regulation of G-protein coupling of some G-protein coupled receptors. G-protein coupled receptors are found in numerous sites within a mammalian host.

Specific G-protein linked receptors have been targeted for the development of drugs for a variety of medical conditions. Over the past 15 years, nearly 150 therapeutic agents targeting 7 transmembrane (7 TM) receptors have been successfully introduced onto the market. This indicates that these receptors have an established, proven history as therapeutic targets.

Molecular cloning and expression of a platelet-activating factor receptor from human leukocytes has been performed (Nakarnura, M., et al. *J. Biol. Chem.*, 1991, 266(30):20400). A G protein coupled receptor induced in activated T cells in chickens has also been identified (Kaplan, M. H. et al., *J Immun.*, 1993, 151:628). Clearly, however, there is a need for identification and characterization of further G protein coupled receptors which play a role in preventing, ameliorating or correcting dysfunctions or diseases.

SUMMARY OF THE INVENTION

Toward these ends, and others, it is an object of the present invention to provide polypeptides, inter alia, that have been identified as novel G-protein coupled receptor HLTEX11 by homology between the amino acid sequence set out in FIG. 1 and known amino acid sequences of other proteins, such as, for example, a chicken G-protein-coupled receptor induced in activated T-cells and a human platelet-activating factor receptor.

It is a further object of the invention, moreover, to provide polynucleotides that encode HLTEX11, particularly polynucleotides that encode the polypeptide herein designated as SEQ ID NO:2.

In a particularly preferred embodiment of this aspect of the invention, the polynucleotide comprises the region encoding human HLTEX11 in the sequence set out in FIGS. 1A and 1B.

In accordance with this aspect of the present invention, there is provided an isolated nucleic acid molecule encoding a mature polypeptide expressible from the human cDNA contained in ATCC Deposit No. 98130.

In accordance with this aspect of the invention, there are provided isolated nucleic acid molecules encoding human HLTEX11, including mRNAs, cDNAs, genomic DNAs and fragments and, in further embodiments of this aspect of the invention, biologically, diagnostically, clinically or therapeutically useful variants, analogs or derivatives thereof, including fragments of the variants, analogs and derivatives.

Among the particularly preferred embodiments of this aspect of the invention are naturally occurring allelic variants of human HLTEX11.

It also is an object of the invention to provide HLTEX11 polypeptides, particularly human HLTEX11 polypeptides, that may be employed for therapeutic purposes, for example, to treat atherosclerosis, inflammatory conditions, and infections, particularly viral infections, such as AIDS, among others.

In accordance with this aspect of the invention, there are provided novel polypeptides of human origin referred to herein as HLTEX11 as well as biologically, diagnostically or therapeutically useful fragments, variants and derivatives thereof, variants and derivatives of the fragments, and analogs of the foregoing.

Among the particularly preferred embodiments of this aspect of the invention are variants of human HLTEX11 encoded by naturally occurring alleles of the human HLTEX11 gene.

In accordance with another aspect of the present invention, there are provided methods of screening for compounds which bind to and activate or inhibit activation of the receptor polypeptides of the present invention and for receptor ligands such as platelet activating factor ("PAF").

It is another object of the invention to provide a process for producing the aforementioned polypeptides, polypeptide fragments, variants and derivatives, fragments of the variants and derivatives, and analogs of the foregoing. In a preferred embodiment of this aspect of the invention, there are provided methods for producing the aforementioned HLTEX11 polypeptides comprising culturing host cells having expressibly incorporated therein an exogenously-derived human HLTEX11-encoding polynucleotide under conditions for expression of human HLTEX11 in the host, expressing the human HLTEX11 in the host cells, and recovering the expressed polypeptide from the host cells.

In accordance with another object of the invention, there are provided products, compositions, processes and methods that utilize the aforementioned polypeptides and polynucleotides for research, biological, clinical and therapeutic purposes, inter alia.

In accordance with certain preferred embodiments of this aspect of the invention, there are provided products, compositions and methods, inter alia, for, among other things: assessing HLTEX11 expression in cells by determining HLTEX11 polypeptides or HLTEX11-encoding mRNA; to treat atherosclerosis, inflammatory conditions, and infections, particularly viral infections, such as AIDS, among others, in vitro, ex vivo or in vivo by exposing cells to HLTEX11 polypeptides or polynucleotides as disclosed herein; assaying genetic variation and aberrations, such as defects, in HLTEX11 genes; and administering a HLTEX11 polypeptide or polynucleotide to an organism to augment HLTEX11 function or remediate HLTEX11 dysfunction.

In accordance with still another embodiment of the present invention, there is provided a process of using such activating compounds to stimulate the receptor polypeptide of the present invention for the treatment of conditions related to the under-expression of HLTEX11.

In accordance with another aspect of the present invention, there is provided a process of using such inhibiting compounds for treating conditions associated with over-expression of the HLTEX11.

In accordance with yet another aspect of the present invention, there is provided non-naturally occurring synthetic, isolated and/or recombinant HLTEX11 polypeptides which are fragments, consensus fragments and/or sequences having conservative amino acid substitutions of at least one domain of the HLTEX11 of the present invention, such that the receptor may bind HLTEX11 ligands, or which may also modulate, quantitatively or qualitatively, HLTEX11 ligand binding.

In accordance with still another aspect of the present invention, there are provided synthetic or recombinant HLTEX11 polypeptides, conservative substitution and derivatives thereof, antibodies thereto, anti-idiotype antibodies, compositions and methods that can be useful as potential modulators of HLTEX11 function, by binding to ligands or modulating ligand binding, due to their expected biological properties, which may be used in diagnostic, therapeutic and/or research applications.

It is still another object of the present invention to provide synthetic, isolated or recombinant polypeptides which are designed to inhibit or mimic various HLTEX11 or fragments thereof, as receptor types and subtypes.

In accordance with certain preferred embodiments of this and other aspects of the invention, there are provided probes that hybridize to human HLTEX11 sequences.

In certain additional preferred embodiments of this aspect of the invention, there are provided antibodies against HLTEX11 polypeptides. In certain particularly preferred embodiments in this regard, the antibodies are highly selective for human HLTEX11.

In accordance with another aspect of the present invention, there are provided HLTEX11 agonists. Among preferred agonists are molecules that mimic HLTEX11, that bind to HLTEX11-binding molecules or receptor molecules, and that elicit or augment HLTEX11-induced responses. Also among preferred agonists are molecules that interact with HLTEX11 or HLTEX11 polypeptides, or with other modulators of HLTEX11 activities, thereby potentiating or augmenting an effect of HLTEX11 or more than one effect of HLTEX11.

In accordance with yet another aspect of the present invention, there are provided HLTEX11 antagonists. Among preferred antagonists are those which mimic HLTEX11 so as to bind to HLTEX11 receptor or binding molecules but not elicit a HLTEX11-induced response or more than one HLTEX11-induced response. Also among preferred antagonists are molecules that bind to or interact with HLTEX11 so as to inhibit an effect of HLTEX11 or more than one effect of HLTEX11 or to prevent expression of HLTEX11.

In a further aspect of the invention, there are provided compositions comprising a HLTEX11 polynucleotide or a HLTEX11 polypeptide for administration to cells in vitro, to cells ex vivo and to cells in vivo, or to a multicellular organism. In certain particularly preferred embodiments of this aspect of the invention, the compositions comprise a HLTEX11 polynucleotide for expression of a HLTEX11 polypeptide in a host organism for treatment of disease. Particularly preferred in this regard is expression in a human patient for treatment of a dysfunction associated with aberrant endogenous activity of HLTEX11.

Other objects, features, advantages and aspects of the present invention will become apparent to those of skill in the art from the following description. It should be understood, however, that the following description and the specific examples, while indicating preferred embodiments of the invention, are given by way of illustration only. Various changes and modifications within the spirit and scope of the disclosed invention will become readily apparent to those skilled in the art from reading the following description and from reading the other parts of the present disclosure.

BRIEF DESCRIPTION OF THE DRAWINGS

The following drawings depict certain embodiments of the invention. They are illustrative only and do not limit the invention otherwise disclosed herein.

FIGS. 1A and 1B show the nucleotide and deduced amino acid sequence of human HLTEX11. FIG. 1A shows the nucleotide sequence of human HLTEX11 (SEQ ID NO:1), while FIG. 1(B) shows the deduced amino acid sequence of HLTEX11 (SEQ ID NO:2).

GLOSSARY

The following illustrative explanations are provided to facilitate understanding of certain terms used frequently herein, particularly in the examples. The explanations are provided as a convenience and are not meant to limit the invention.

"Digestion" of DNA refers to catalytic cleavage of a DNA with an enzyme such as, but not limited to, a restriction enzyme that acts only at certain sequences in the DNA. The various restriction enzymes referred to herein are commercially available and their reaction conditions, cofactors and other requirements for use are known and routine to the skilled artisan.

For analytical purposes, typically, 1 microgram of plasmid or DNA fragment is gested with about 2 units of enzyme in about 20 microliters of reaction buffer. For the purpose of isolating DNA fragments for plasmid construction, typically 5 to 50 micrograms of DNA are digested with 20 to 250 units of enzyme in proportionately larger volumes.

Appropriate buffers and substrate amounts for particular restriction enzymes are described in standard laboratory manuals, such as those referenced below, and are specified by commercial suppliers.

Incubation times of about 1 hour at 37° C. are ordinarily used, but conditions may vary in accordance with standard procedures, the supplier's instructions and the particulars of the reaction. After digestion, reactions may be analyzed, and fragments may be purified by electrophoresis through an agarose or polyacrylamide gel, using well known methods that are routine for those skilled in the art.

"Genetic element" generally means a polynucleotide comprising a region that encodes a polypeptide or a region that regulates replication, transcription, translation or other processes important to expression of the polypeptide in a host cell, or a polynucleotide comprising both a region that encodes a polypeptide and a region operably linked thereto that regulates expression.

Genetic elements may be comprised within a vector that replicates as an episomal element; that is, as a molecule physically independent of the host cell genome. They may be comprised within mini-chromosomes, such as those that arise during amplification of transfected DNA by methotrexate selection in eukaryotic cells. Genetic elements also may be comprised within a host cell genome, not in their natural state but, rather, following manipulation such as isolation, cloning and introduction into a host cell in the form of purified DNA or in a vector, among others.

"Isolated" means altered "by the hand of man" from its natural state; i.e., that, if it occurs in nature, it has been changed or removed from its original environment, or both. For example, a naturally occurring polynucleotide or a polypeptide naturally present in a living animal in its natural state is not "isolated," but the same polynucleotide or polypeptide separated from the coexisting materials of its natural state is "isolated", as the term is employed herein. For example, with respect to polynucleotides, the term isolated means that it is separated from the chromosome and cell in which it naturally occurs.

As part of or following isolation, such polynucleotides can be joined to other polynucleotides such as DNAs for mutagenesis, to form fusion proteins, and for propagation or expression in a host, for instance. The isolated polynucleotides, alone or joined to other polynucleotides such as vectors, can be introduced into host cells, in culture or in whole organisms. Introduced into host cells in culture or in whole organisms, such DNAs still would be isolated, as the term is used herein, because they would not be in their naturally occurring form or environment. Similarly, the polynucleotides and polypeptides may occur in a composition, such as a media, formulations, solutions for introduction of polynucleotides or polypeptides, for example, into cells, compositions or solutions for chemical or enzymatic reactions, for instance, which are not naturally occurring compositions, and, therein remain isolated polynucleotides or polypeptides within the meaning of that term as it is employed herein.

"Ligation" refers to the process of forming phosphodiester bonds between two or more polynucleotides, which most often are double stranded DNAs. Techniques for ligation are well known to the art and protocols for ligation are described in standard laboratory manuals and references, such as, for instance, Sambrook et al., MOLECULAR CLONING, A LABORATORY MANUAL, 2nd Ed.; Cold Spring Harbor Laboratory Press, Cold Spring Harbor, N.Y., 1989, hereinafter referred to as Sambrook et al.

"Oligonucleotide(s)" refers to relatively short polynucleotides. Often the term refers to single-stranded deoxyribonucleotides, but it can refer as well to single- or double-stranded ribonucleotides, RNA:DNA hybrids and double-stranded DNAs, among others.

Oligonucleotides, such as single-stranded DNA probe oligonucleotides, often are synthesized by chemical methods, such as those implemented on automated oligonucleotide synthesizers. However, oligonucleotides can be made by a variety of other methods, including in vitro recombinant DNA-mediated techniques and by expression of DNAs in cells and organisms.

Initially, chemically synthesized DNAs typically are obtained without a 5' phosphate. The 5' ends of such oligonucleotides are not substrates for phosphodiester bond formation by ligation reactions that employ DNA ligases typically used to form recombinant DNA molecules. Where ligation of such oligonucleotides is desired, a phosphate can be added by standard techniques, such as those that employ a kinase and ATP.

The 3' end of a chemically synthesized oligonucleotide generally has a free hydroxyl group and, in the presence of a ligase, such as T4 DNA ligase, will readily form a phosphodiester bond with a 5' phosphate of another polynucleotide, such as another oligonucleotide. As is well known, this reaction can be prevented selectively, where desired, by removing the 5' phosphates of the other polynucleotide(s) prior to ligation.

"Plasmids" are genetic elements that are stably inherited without being a part of the chromosome of their host cell. They may be comprised of DNA or RNA and may be linear or circular. Plasmids code for molecules that ensure their replication and stable inheritance during cell replication and may encode products of considerable medical, agricultural and environmental importance. For example, they code for toxins that greatly increase the virulence of pathogenic bacteria. They can also encode genes that confer resistance to antibiotics. Plasmids are widely used in molecular biology as vectors used to clone and express recombinant genes. Plasmids generally are designated herein by a lower case "p" preceded and/or followed by capital letters and/or numbers, in accordance with standard naming conventions that are familiar to those of skill in the art. Starting plasmids disclosed herein are either commercially available, publicly available, or can be constructed from available plasmids by routine application of well known, published procedures. Many plasmids and other cloning and expression vectors that can be used in accordance with the present invention are well known and readily available to those of skill in the art. Moreover, those of skill may readily construct any number of other plasmids suitable for use in the invention. The properties, construction and use of such plasmids, as well as other vectors, in the present invention will be readily apparent to those of skill from the present disclosure.

"Polynucleotide(s)" generally refers to any polyribonucleotide or polydeoxribonucleotide, which may be unmodified RNA or DNA or modified RNA or DNA. Thus, for instance, polynucleotides as used herein refers to, among others, single-and double-stranded DNA, DNA that is a mixture of single- and double-stranded regions, single- and double-stranded RNA, and RNA that is mixture of single- and double-stranded regions, hybrid molecules comprising DNA and RNA that may be single-stranded or, more typically, double-stranded or a mixture of single- and double-stranded regions. In addition, polynucleotide, as used herein, refers to triple-stranded regions comprising RNA or DNA or both RNA and DNA. The strands in such regions may be from the same molecule or from different molecules. The regions may include all of one or more of the molecules, but more typically involve only a region of some of the molecules. One of the molecules of a triple-helical region often is an oligonucleotide. As used herein, the term polynucleotide also includes DNAs or RNAs as described above that contain one or more modified bases. Thus, DNAs or RNAs with backbones modified for stability or for other reasons are polynucleotides, as that term is intended herein. Moreover, DNAs or RNAs comprising unusual bases, such as inosine, or modified bases, such as tritylated bases, to name just two examples, are polynucleotides, as the term is used herein. It will be appreciated that a great variety of modifications have been made to DNA and RNA that serve many useful purposes known to those of skill in the art. The term polynucleotide, as it is employed herein, embraces such chemically, enzymatically or metabolically modified forms of polynucleotides, as well as the chemical forms of DNA and RNA characteristic of viruses and cells, including inter alia simple and complex cells.

"Polypeptides", as used herein, includes all polypeptides as described below. The basic structure of polypeptides is well known and has been described in innumerable textbooks and other publications in the art. In this context, the term is used herein to refer to any peptide or protein comprising two or more amino acids joined to each other in a linear chain by peptide bonds. As used herein, the term refers to both short chains, which also commonly are referred to in the art as peptides, oligopeptides and oligomers, for example, and to longer chains, which generally are referred to in the art as proteins, of which there are many types.

It will be appreciated that polypeptides often contain amino acids other than the 20 amino acids commonly referred to as the 20 naturally occurring amino acids, and that many amino acids, including the terminal amino acids, may be modified in a given polypeptide, either by natural processes, such as processing and other post-translational modifications, or by chemical modification techniques which are well known to the art. Even the common modifications that occur naturally in polypeptides are too numerous to list exhaustively here, but they are well described in basic texts and in more detailed monographs, as well as in a voluminous research literature, and thus are well known to those of skill in the art.

Known modifications which may be present in polypeptides of the present invention include, but are not limited to, acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent cross-links, formation of cystine, formation of pyroglutamate, formylation, gamma-carboxylation, glycosylation, GPI anchor formation, hydroxylation, iodination, methylation, myristoylation, oxidation, proteolytic processing, phosphorylation, prenylation, racemization, selenoylation, sulfation, transfer-RNA mediated addition of amino acids to proteins such as arginylation, and ubiquitination. Such modifications are well known to those of skill and have been described in great detail in the scientific literature. Several particularly common modifications including glycosylation, lipid attachment, sulfation, garnma-carboxylation of glutamic acid residues, hydroxylation and ADP-ribosylation are described in most basic texts such as PROTEINS—STRUCTURE AND MOLECULAR PROPERTIES, 2nd Ed., T. E. Creighton, W. H. Freeman and Company, New York, 1993. Detailed reviews are also available on this subject. See, e.g. Wold, F., Posttranslational Protein Modifications: Perspectives and Prospects, page. 1–12 in POSTTRANSLATIONAL COVALENT MODIFICATION OF PROTEINS, B. C. Johnson, Ed., Academic Press, New York, 1983; Seifter et al., "Analysis for protein modifications and nonprotein cofactors", *Meth. Enzymol.*, 1990, 182:626–646 and Rattan et al, "Protein Synthesis: Posttranslational Modifications and Aging", *Ann. N.Y Acad. Sci.*, 1992, 663: 48–62.

It will be appreciated, as is well known and as noted above, that polypeptides are not always entirely linear. For instance, polypeptides may be branched as a result of ubiquitination, and they may be circular, with or without branching, generally as a result of posttranslation events, including natural processing event and events brought about by human manipulation which do not occur naturally. Circular, branched and branched circular polypeptides may be synthesized by non-translation natural processes or by entirely synthetic methods, as well.

Modifications can occur anywhere in a polypeptide, including the peptide backbone, the amino acid side-chains and the amino or carboxyl termini. In fact, blockage of the amino or carboxyl group in a polypeptide, or both, by a covalent modification, is common in naturally occurring and synthetic polypeptides and such modifications may be present in polypeptides of the present invention, as well. For instance, the amino terminal residue of polypeptides made in E. coli, prior to processing, almost invariably will be N-formylmethionine.

The modifications that occur in a polypeptide often will be a function of how it is made. For polypeptides made by expressing a cloned gene in a host, for instance, the nature and extent of the modifications in large part will be determined by the host cell's posttranslational modification capacity and the modification signals present in the polypeptide amino acid sequence. For instance, as is well known, glycosylation often does not occur in bacterial hosts such as E. coli. Accordingly, when glycosylation is desired, a polypeptide should be expressed in a glycosylating host, generally a eukaryotic cell. Insect cells often carry out the same posttranslational glycosylations as mammalian cells and, for this reason, insect cell expression systems have been developed to express efficiently mammalian proteins having the native patterns of glycosylation, inter alia. Similar considerations apply to other modifications.

It will be appreciated that the same type of modification may be present in the same or varying degrees at several sites in a given polypeptide. Also, a given polypeptide may contain many types of modifications.

In general, as used herein, the term polypeptide encompasses all such modifications, particularly those that are present in polypeptides synthesized by expressing a polynucleotide in a host cell.

"Variant(s)" of polynucleotides or polypeptides, as the term is used herein, are polynucleotides or polypeptides that differ from a reference polynucleotide or polypeptide, respectively. Variants in this sense are described below and elsewhere in the present disclosure in greater detail. Variants include polynucleotides that differ in nucleotide sequence from another, reference polynucleotide. Generally, differences are limited so that the nucleotide sequences of the reference and the variant are closely similar overall and, in many regions, identical.

As noted below, changes in the nucleotide sequence of the variant may be silent. That is, they may not alter the amino acids encoded by the polynucleotide. Where alterations are limited to silent changes of this type, a variant will encode a polypeptide with the same amino acid sequence as the reference. As also noted below, changes in the nucleotide sequence of the variant may alter the amino acid sequence of a polypeptide encoded by the reference polynucleotide. Such nucleotide changes may result in amino acid substitutions, additions, deletions, fusions and truncations in the polypeptide encoded by the reference sequence, as discussed below.

Variants also include polypeptides that differ in amino acid sequence from another, reference polypeptide. Generally, differences are limited so that the sequences of the reference and the variant are closely similar overall and, in many regions, identical.

A variant and reference polypeptide may differ in amino acid sequence by one or more substitutions, additions, deletions, fusions and truncations, which may be present in any combination.

"Fusion protein" as the term is used herein, is a protein encoded by two, often unrelated, fused genes or fragments thereof. EP-A-O 464 533 (Canadian counterpart 2045869) discloses fusion proteins comprising various portions of constant region of immunoglobin molecules together with another human protein or part thereof. In many cases, employing an immunoglobulin Fc region as a part of a fusion protein is advantageous for use in therapy and diagnosis resulting in, for example, improved pharmacokinetic properties (EP-A 0232 262). On the other hand, for some uses it would be desirable to be able to delete the Fc part after the fusion protein has been expressed, detected and purified. Accordingly, it may be desirable to link the components of the fusion protein with a chemically or enzymatically cleavable linking region. This is the case when the Fc portion proves to be a hindrance to use in therapy and diagnosis, for example, when the fusion protein is to be used as an antigen for immunizations. In drug discovery, for example, human proteins, such as, shIL5-α have been fused with Fc portions for use in high-throughput screening assays to identify antagonists of hIL-5. See, D. Bennett et al., Journal of Molecular Recognition, 1995, 8:52–58; and K. Johanson et al., The Journal of Biological Chemistry, 1995, 270(16):9459–9471.

Thus, this invention also relates to genetically engineered soluble fusion proteins comprised of HLTEX11, or a portion thereof, and of various portions of the constant regions of heavy or light chains of immunoglobulins of various subclasses (IgG, IgM, IgA, IgE). Preferred as an immunoglobulin is the constant part of the heavy chain of human IgG, particularly IgG1, where fusion takes place at the hinge region. In one embodiment, the Fc part can be removed simple by incorporation of a cleavage sequence which can be cleaved with blood clotting factor Xa. This invention further relates to processes for the preparation of these fusion proteins by genetic engineering, and to the use thereof for diagnosis and therapy. Yet a further aspect of the invention relates to polynucleotides encoding such fusion proteins.

Membrane bound receptors are particularly useful in the formation of fusion proteins. Such receptors are generally characterized as possessing three distinct structural regions; an extracellular domain, a transmembrane domain, and a cytoplasmic domain. This invention contemplates the use of one or more of these regions as components of a fusion protein. Examples of such fusion protein technology can be found in WO94/29458 and WO94/22914.

"Binding molecules" (or otherwise called "interaction molecules" or "receptor component factors") refer to molecules, including ligands, that specifically bind to or interact with receptor polypeptides of the present invention. Such binding molecules are a part of the present invention. Binding molecules may also be non-naturally occurring, such as antibodies and antibody-derived reagents that bind specifically to polypeptides of the invention.

As known in the art, "similarity" between two polypeptides is determined by comparing the amino acid sequence and its conserved amino acid substitutes of one polypeptide to the sequence of a second polypeptide. Moreover, also known in the art is "identity", which means the degree of sequence relatedness between two polypeptide or two polynucleotide sequences as determined by the identity of the match between two strings of such sequences. Both identity and similarity can be readily calculated (COMPUTATIONAL MOLECULAR BIOLOGY, Lesk, A. M., ed., Oxford University Press, New York, 1988; BIOCOMPUTING: INFORMATICS AND GENOME PROJECTS, Smith, D. W., ed., Academic Press, New York, 1993; COMPUTER ANALYSIS OF SEQUENCE DATA, PART I, Griffin, A. M., and Griffin, H. G., eds., Humana Press, New Jersey, 1994; SEQUENCE ANALYSIS IN MOLECULAR BIOLOGY, von Heinje, G., Academic Press, 1987; and SEQUENCE ANALYSIS PRIMER, Gribskov, M. and Devereux, J., eds., M Stockton Press, New York, 1991). There exist a number of methods to measure identity and similarity between two polynucleotide or polypeptide sequences and the terms "identity" and "similarity" are well known to skilled artisans (Carillo, H., and Lipton, D., *SIAM J. Applied Math.*, 1988, 48:1073). Methods commonly employed to determine identity or similarity between two sequences include, but are not limited to, those disclosed in GUIDE TO HUGE COMPUTERS, Martin J. Bishop, ed., Academic Press, San Diego, 1994, and Carillo, H., and Lipton, D., *SIAM J. Applied Math.*, 1988, 48:1073. Preferred methods to determine identity are designed to give the largest match between the two sequences tested. Methods to determine identity and similarity are also codified in computer programs. Preferred computer program methods to determine identity and similarity between two sequences include, but are not limited to, GCG program package (Devereux, J., et al., *Nucleic Acids Research*, 1984, 12(1):387), BLASTP, BLASTN, FASTA (Atschul, S. F. et al., *J Molec. Biol.*, 1990, 215:403).

DETAILED DESCRIPTION OF THE INVENTION

The present invention relates to novel HLTEX11 polypeptides and polynucleotides, among other things, as described in greater detail below. In particular, the invention relates to polypeptides and polynucleotides of a novel human HLTEX11, which is related by amino acid sequence homology to chicken G-protein-coupled receptor induced in activated T-cells and to a human platelet-activating factor receptor polypeptides. The invention relates especially to HLTEX11 having the nucleotide and amino acid sequences set out in FIG. 1, and to the HLTEX11 nucleotide sequences of the human cDNA in ATCC DEPOSIT NO. 98130, herein referred to as "the deposited clone" or as the "cDNA of the deposited clone", and amino acid sequences encoded thereby. It will be appreciated that the nucleotide and amino acid sequences set out in FIGS. 1A and 1B were obtained by sequencing the cDNA of the deposited clone. Hence, the sequence of the deposited clone is controlling as to any discrepancies between the two and any reference to the sequences of FIGS. 1A and 1B includes a reference to the sequence of the human cDNA of the deposited clone.

Polynucleotides

In accordance with one aspect of the present invention, there are provided isolated polynucleotides which encode the HLTEX11 polypeptide having the deduced amino acid sequence of FIG. 1B.

Using the information provided herein, such as the polynucleotide sequence set out in FIG. 1A, a polynucleotide of the present invention encoding human HLTEX11 may be obtained using standard cloning and screening procedures, such as those for cloning cDNAs using mRNA from cells from the spleen or testes as starting material. Illustrative of the invention, the full-length HLTEX11 gene was isolated from a human spleen plasmid cDNA library. A partial sequence was initially derived from a cDNA library prepared from a human T-cell lymphoma cDNA library. Using this sequence primers were designed near the 5' end of the partial clone to isolate the full length clone. A 3' primer was also made and used in conjunction with the 5' primer to screen nine different human tissue plasmid cDNA libraries. Of these, only the spleen and testis libraries contains the HLTEX11 gene.

Human HLTEX11 of the invention is structurally related to other proteins expressed in activated T cells and in platelets, as shown by the results of sequencing the cDNA encoding human HLTEX11 in the deposited clone. The cDNA sequence thus obtained is set out in FIG. 1A. It contains an open reading frame encoding a protein of about 339 amino acid residues with a deduced molecular weight of about 38 kDa. The first approximately 20 amino acids represent a putative leader sequence. The protein exhibits greatest homology to a chicken G-protein-coupled receptor induced in activated T-cells and to a human platelet-activating factor receptor protein among known proteins. HLTEX11 of FIG. 1B has about 34% identity and 56% similarity with the entire gene sequence of a chicken G-protein-coupled receptor induced in activated T-cells and has about 36% identity and 54% similarity with the entire gene sequence of a human platelet-activating factor receptor.

Polynucleotides of the present invention may be in the form of RNA, such as mRNA, or in the form of DNA, including, for instance, cDNA and genomic DNA obtained by cloning or produced by chemical synthetic techniques or by a combination thereof. The DNA may be double-stranded or single-stranded. Single-stranded DNA may be the coding strand, also known as the sense strand, or it may be the non-coding strand, also referred to as the antisense strand.

The coding sequence which encodes the polypeptide may be identical to the coding sequence of the polynucleotide shown in FIG. 1A, SEQ ID NO: 1. It also may be a polynucleotide with a different sequence, which, as a result of the redundancy (degeneracy) of the genetic code, also encodes the polypeptide of FIG. 1B, SEQ ID NO: 2.

Polynucleotides of the present invention which encode the polypeptide of FIG. 1 may include, but are not limited to, the coding sequence for the mature polypeptide by itself; the coding sequence for the mature polypeptide and additional coding sequences; and the coding sequence of the mature polypeptide, with or without the aforementioned additional coding sequences, together with additional, non-coding sequences. Examples of additional coding sequences include, but are not limited to , sequences encoding a leader or secretory sequence, such as a pre-, or pro- or preproprotein sequence. Examples of additional non-coding sequences include, but not limited to, introns and non-coding 5' and 3' sequences, such as the transcribed, non-translated sequences that play a role in transcription and mRNA processing, including splicing and polyadenylation signals, for example, for ribosome binding and stability of mRNA. Coding sequences which provide additional functionalities may also be incorporated into the polypeptide. Thus, for instance, the polypeptide may be fused to a marker sequence, such as a peptide, which facilitates purification of the fused polypeptide. In certain preferred embodiments of this aspect of the invention, the marker sequence is a hexa-histidine peptide, such as that provided in the pQE vector (Qiagen, Inc.). As described in Gentz et al, *Proc. Natl Acad. Sci., USA*, 1989, 86:821–824, for instance, hexa-histidine provides for convenient purification of the fusion protein. The HA tag corresponds to an epitope derived of influenza hemagglutinin protein, which has been described, for instance, by Wilson et al, *Cell*, 1984, 37:767. Many other such tags are commercially available.

In accordance with the foregoing, the term "polynucleotide encoding a polypeptide" as used herein encompasses polynucleotides which include, by virtue of the redundancy of the genetic code, any sequence encoding a polypeptide of the present invention, particularly the human HLTEX11 having the amino acid sequence set out in FIG. 1B. The term also encompasses polynucleotides that include a single continuous region or discontinuous regions encoding the polypeptide (for example, interrupted by introns) together with additional regions, that may also contain coding and/or non-coding sequences.

The present invention further relates to variants of the herein above described polynucleotides which encode for fragments, analogs and derivatives of the polypeptide having the deduced amino acid sequence of FIG. 1B. A variant of the polynucleotide may be a naturally occurring variant such as a naturally occurring allelic variant, or it may be a variant that is not known to occur naturally. Such non-naturally occurring variants of the polynucleotide may be made by mutagenesis techniques, including those applied to polynucleotides, cells or organisms.

Among variants in this regard are variants that differ from the aforementioned polynucleotides by nucleotide substitutions, deletions or additions. The substitutions, deletions or additions may involve one or more nucleotides. The variants may be altered in coding or non-coding regions or both. Alterations in the coding regions may produce conservative or non-conservative amino acid substitutions, deletions or additions.

Among the particularly preferred embodiments of the invention in this regard are polynucleotides encoding polypeptides having the amino acid sequence of HLTEX11 set out in FIG. 1B; variants, analogs, derivatives and fragments thereof, and fragments of the variants, analogs and derivatives. Further particularly preferred in this regard are polynucleotides encoding HLTEX11 variants, analogs, derivatives and fragments, and variants, analogs and derivatives of the fragments, which have the amino acid sequence of the HLTEX11 polypeptide of FIG. 1B in which several, a few, 5 to 10, 1 to 5, 1 to 3, 2, 1 or no amino acid residues are substituted, deleted or added, in any combination. Especially preferred among these are silent substitutions, additions and deletions, which do not alter the properties and activities of the HLTEX11. Also especially preferred in this regard are conservative substitutions. Most highly preferred are polynucleotides encoding polypeptides having the amino acid sequence of FIG. 1B, without substitutions.

Further preferred embodiments of the invention are polynucleotides that are at least 70% identical to a polynucleotide encoding the HLTEX11 polypeptide having the amino acid sequence set out in FIG. 1B, and polynucleotides which are complementary to such polynucleotides. More preferred are polynucleotides that comprise a region that is at least 80% identical to a polynucleotide encoding the HLTEX11 polypeptide of the human cDNA of the deposited clone and polynucleotides complementary thereto. In this regard, polynucleotides at least 90% identical to the same are particularly preferred, and those with at least 95% are more particularly preferred. Furthermore, those with at least 97% are highly preferred and those with at least 98–99% are most highly preferred, with at least 99% being the most preferred.

Particularly preferred embodiments, in this respect, are polynucleotides which encode polypeptides which retain substantially the same biological function or activity as the mature polypeptide encoded by the cDNA of FIG. 1A.

The present invention further relates to polynucleotides that hybridize to the herein above-described sequences. In this regard, the present invention relates to polynucleotides which hybridize under stringent conditions to the herein above-described polynucleotides. As used herein, the term "stringent conditions" means hybridization will occur only if there is at least 95% and preferably at least 97% identity between the sequences.

The polynucleotides may encode a polypeptide which is the mature protein plus additional amino or carboxyl-terminal amino acids, or amino acids interior to the mature polypeptide (when the mature form has more than one polypeptide chain, for instance). Such sequences may play a role in processing of a protein from precursor to a mature form, may facilitate protein trafficking, may prolong or shorten protein half-life or may facilitate manipulation of a protein for assay or production, among other things. As generally is the case in situ, the additional amino acids may be processed away from the mature protein by cellular enzymes. A precursor protein, having the mature form of the polypeptide fused to one or more prosequences may be an inactive form of the polypeptide. When prosequences are removed such inactive precursors generally are activated. Some or all of the prosequences may be removed before activation. Generally, such precursors are called proproteins.

In sum, a polynucleotide of the present invention may encode a mature protein, a mature protein plus a leader sequence (which may be referred to as a preprotein), a precursor of a mature protein having one or more prosequences which are not the leader sequences of a preprotein, or a preproprotein, which is a precursor to a proprotein, having a leader sequence and one or more prosequences, which generally are removed during processing steps that produce active and mature forms of the polypeptide.

Deposited materials

A deposit containing human HLTEX11 cDNA was made with the American Type Culture Collection, 12301 Park Lawn Drive, Rockville, Md. 20852, USA, on Aug. 8, 1996, and assigned ATCC Deposit No. 98130. The human cDNA deposit is referred to herein as "the deposited clone" or as "the cDNA of the deposited clone."

The deposited material comprises *E. coli* pCMVSport HLTEX11, strain MM294, and contains the full length HLTEX11 cDNA.

The deposit has been made under the terms of the Budapest Treaty on the international recognition of the deposit of micro-organisms for purposes of patent procedure. The strain will be irrevocably and without restriction or condition released to the public upon the issuance of a patent. The deposit is provided merely as convenience to those of skill in the art and is not an admission that a deposit is required for enablement, such as that required under 35 U.S.C. § 112.

The sequence of the polynucleotides contained in the deposited material, as well as the amino acid sequence of the polypeptide encoded thereby, are controlling in the event of any conflict with any description of sequences herein.

A license may be required to make, use or sell the deposited materials. No such license is hereby granted.

Polypeptides

The present invention further relates to a human HLTEX11 polypeptide which has the deduced amino acid sequence of FIG. 1B, SEQ ID NO:2.

The invention also relates to fragments, analogs and derivatives of this polypeptide. The terms "fragment," "derivative" and "analog" when referring to the polypeptide of FIG. 1, mean a polypeptide which retains essentially the same biological function or activity as such polypeptide, i.e. functions as HLTEX11, or retains the ability to bind the ligand or the binding molecules even though the polypeptide does not function as HLTEX11, for example, a soluble form of the receptor. Thus, an analog includes, for example, a proprotein which can be activated by cleavage of the proprotein portion to produce an active mature polypeptide.

The polypeptide of the present invention may be a recombinant polypeptide, a natural polypeptide or a synthetic polypeptide. In certain preferred embodiments, it is a recombinant polypeptide.

The fragment, derivative or analog of the polypeptide of FIG. 1B may be (i) one in which one or more of the amino acid residues are substituted with a conserved or non-conserved amino acid residue (preferably a conserved amino acid residue) and such substituted amino acid residue may or may not be one encoded by the genetic code; (ii) one in which one or more of the amino acid residues includes a substituent group; (iii) one in which the mature polypeptide is fused with another compound, such as a compound to increase the half-life of the polypeptide (for example, polyethylene glycol); or (iv) one in which the additional amino acids are fused to the mature polypeptide, such as a leader or secretory sequence or a sequence which is employed for purification of the mature polypeptide or a proprotein sequence. Such fragments, derivatives and analogs are deemed to be within the scope of the instant invention as production of such fragments, derivatives and analogs is routine to those skilled in the art based upon the teachings herein.

Among the particularly preferred embodiments of the invention in this regard are polypeptides having the amino acid sequence of HLTEX11 set out in FIG. 1B, variants, analogs, derivatives and fragments thereof, and variants, analogs and derivatives of the fragments. Further particularly preferred embodiments of the invention in this regard are polypeptides having the amino acid sequence of HLTEX11, variants, analogs, derivatives and fragments thereof, and variants, analogs and derivatives of the fragments which retain the activity and/or finction of HLTEX11.

Among preferred variants are those that vary from a reference by conservative amino acid substitutions. Such substitutions are those that substitute a given amino acid in a polypeptide by another amino acid of like characteristics. Typically seen as conservative substitutions are the replacements, one for another, among the aliphatic amino acids Ala, Val, Leu and Ile; interchange of the hydroxyl residues Ser and Thr, exchange of the acidic residues Asp and Glu, substitution between the amide residues Asn and Gln, exchange of the basic residues Lys and Arg and replacements among the aromatic residues Phe and Tyr.

Further particularly preferred in this regard are variants, analogs, derivatives and fragments, and variants, analogs and derivatives of the fragments, having the amino acid sequence of the HLTEX11 polypeptide of FIG. 1, in which several, a few, 5 to 10, 1 to 5, 1 to 3, 2, 1 or no amino acid residues are substituted, deleted or added, in any combination. Especially preferred among these are silent substitutions, additions and deletions, which do not alter the properties and activities of HLTEX11. Also especially preferred in this regard are conservative substitutions. Most highly preferred are polypeptides having the amino acid sequence of FIG. 1B without substitutions.

The polypeptides and polynucleotides of the present invention are preferably provided in an isolated form, and more preferably are purified to homogeneity.

The polypeptides of the present invention include the polypeptide of SEQ ID NO: 2 (in particular the mature polypeptide) as well as polypeptides which have at least 70% identity to the polypeptide of SEQ ID NO: 2 and more preferably at least 90% similarity (more preferably at least 90% identity) to the polypeptide of SEQ ID NO: 2 and still more preferably at least 95% similarity (still more preferably at least 95% identity) to the polypeptide of SEQ ID NO: 2 and also include portions of such polypeptides with such portion of the polypeptide generally containing at least 30 amino acids and more preferably at least 50 amino acids.

Fragments or portions of the polypeptides of the present invention may be employed for producing the corresponding fiull-length polypeptide by peptide synthesis; therefore, the fragments may be employed as intermediates for producing the full-length polypeptides. Fragments or portions of the polynucleotides of the present invention may be used to synthesize full-length polynucleotides of the present invention. Fragments may be "free-standing," i.e., not part of or fused to other amino acids or polypeptides, or they may be comprised within a larger polypeptide of which they form a part or region. When comprised within a larger polypeptide, the presently discussed fragments most preferably form a single continuous region. However, several fragments may be comprised within a single larger polypeptide. For instance, certain preferred embodiments relate to a fragment of a HLTEX11 polypeptide of the present comprised within a precursor polypeptide designed for expression in a host and having heterologous pre- and pro-polypeptide regions fused to the amino terminus of the HLTEX11 fragment and an additional region fused to the carboxyl terminus of the fragment. Therefore, fragments in one aspect of the meaning intended herein, refers to the portion or portions of a fusion polypeptide or fusion protein derived from HLTEX11.

As representative examples of polypeptide fragments of the invention, there may be mentioned those which have from about 5–15, 10–20, 15–40, 30–55, 41–75, 41–80, 41–90, 50–100, 75–100, 90–115, 100–125, and 110–113 amino acids in length.

In this context "about" includes the particularly recited range and ranges larger or smaller by several, a few, 5, 4, 3, 2 or 1 amino acid residues at either extreme or at both extremes. For instance, about 40–90 amino acids in this context means a polypeptide fragment of 40 plus or minus several, a few, 5, 4, 3, 2 or 1 amino acid residues to 90 plus or minus several a few, 5, 4, 3, 2 or 1 amino acid residues, i.e., ranges as broad as 40 minus several amino acids to 90 plus several amino acids to as narrow as 40 plus several amino acids to 90 minus several amino acids. Highly preferred in this regard are the recited ranges plus or minus as many as 5 amino acids at either or at both extremes. Particularly highly preferred are the recited ranges plus or minus as many as 3 amino acids at either or at both the recited extremes. Especially particularly highly preferred are ranges plus or minus 1 amino acid at either or at both extremes or the recited ranges with no additions or deletions. Most highly preferred of all in this regard are fragments from about 5–15, 10–20, 15–40, 30–55, 41–75, 41–80, 41–90, 50–100, 75–100, 90–115, 100–125, and 110–113 amino acids long.

Among especially preferred fragments of the invention are truncation mutants of HLTEX11. Truncation mutants include HLTEX11 polypeptides having the amino acid sequence of FIGS. 1A and 1B, or of variants or derivatives thereof, except for deletion of a continuous series of residues (that is, a continuous region, part or portion) that includes the amino terminus, or a continuous series of residues that includes the carboxyl terminus or, as in double truncation mutants, deletion of two continuous series of residues, one including the amino terminus and one including the carboxyl terminus. Particularly preferred fragments of the membrane bound receptors of this invention include soluble forms of the receptor comprising the extracellular domain, without its attendant transmembrane and cytoplasmic domains, and transmembrane region deletions wherein the extracellular domain is fused directly to the cytoplasmic domain. See for example, published PCT application number WO94/03620. Alternatively, the fragments of the present invention may include deletion of the transmembrane region only and retention of at least part of the cytoplasmic domain itself or fusion with at least part of an alternate cytoplasmic domain as described in WO96/04382. Fragments having the size ranges set out above are also preferred embodiments of truncation fragments, which are especially preferred among fragments generally.

Also preferred in this aspect of the invention are fragments characterized by structural or functional attributes of HLTEX11. Preferred embodiments of the invention in this regard include fragments that comprise alpha-helix and alpha-helix forming regions ("alpha-regions"), beta-sheet and beta-sheet-forming regions ("beta-regions"), turn and turn-forming regions ("turn-regions"), coil and coil-forming regions ("coil-regions"), hydrophilic regions, hydrophobic regions, alpha amphipathic regions, beta amphipathic regions, flexible regions, surface-forming regions and high antigenic index regions of HLTEX11.

Among highly preferred fragments in this regard are those that comprise regions of HLTEX11 that combine several structural features, such as several of the features set out above. In this regard, the regions defined by the residues about 10 to about 20, about 40 to about 50, about 70 to about 90 and about 100 to about 113 of FIGS. 1A and 1B, which all are characterized by amino acid compositions highly characteristic of turn-regions, hydrophilic regions, flexible-regions, surface-forming regions, and high antigenic index-regions, are especially highly preferred regions. Such regions may be comprised within a larger polypeptide or may be by themselves a preferred fragment of the present invention, as discussed above. It will be appreciated that the term "about" as used in this paragraph has the meaning set out above regarding fragments in general.

Further preferred regions are those that mediate activities of HLTEX11. Most highly preferred in this regard are fragments that have a chemical, biological or other activity of HLTEX11, including those with a similar activity or an improved activity, or with a decreased undesirable activity. Highly preferred in this regard are fragments that contain regions that are homologs in sequence, or in position, or in both sequence and position, to active regions of related polypeptides, such as a chicken G-protein-coupled receptor induced in activated T-cells and a human platelet-activating factor receptor.

It will be appreciated that the invention also relates to, among others, polynucleotides encoding the aforementioned fragments, polynucleotides that hybridize to polynucleotides encoding the fragments, particularly those that hybridize under stringent conditions, and polynucleotides, such as PCR primers, for amplifying polynucleotides that encode the fragments. In these regards, preferred polynucleotides are those that correspond to the preferred fragments, as discussed above.

Vectors, host cells, expression

The present invention also relates to vectors which contain polynucleotides of the present invention, host cells which are genetically engineered with vectors of the invention and the production of polypeptides of the invention by recombinant techniques.

Host cells can be genetically engineered to incorporate polynucleotides and express polypeptides of the present invention. For instance, polynucleotides may be introduced into host cells using well known techniques of infection, transduction, transfection, transvection and transformation. The polynucleotides may be introduced alone or with other polynucleotides. Such other polynucleotides may be introduced independently, co-introduced or introduced joined to the polynucleotides of the invention. Thus, for instance, polynucleotides of the invention may be transfected into host cells with another, separate polynucleotide encoding a selectable marker, using standard techniques for co-transfection and selection in, for instance, mammalian cells. In this embodiment, the polynucleotides generally will be stably incorporated into the host cell genome.

Alternatively, the polynucleotides may be joined to a vector containing a selectable marker for propagation in a host. The vector construct may be introduced into host cells by the aforementioned techniques. Generally, a plasmid vector is introduced as DNA in a precipitate, such as a calcium phosphate precipitate, or in a complex with a charged lipid. Electroporation may also be used to introduce polynucleotides into a host. If the vector is a virus, it may be packaged in vitro or introduced into a packaging cell and the packaged virus may be transduced into cells. A wide variety of techniques suitable for making polynucleotides and for introducing polynucleotides into cells in accordance with this aspect of the invention are well known and routine to those of skill in the art. Such techniques are reviewed at length in Sambrook et al. which is merely illustrative of the many laboratory manuals that detail these techniques.

In accordance with this aspect of the invention the vector may be, for example, a plasmid vector, a single or double-stranded phage vector, or a single or double-stranded RNA or DNA viral vector. Such vectors may be introduced into cells as polynucleotides, preferably DNA, by well known techniques for introducing DNA and RNA into cells. The vectors, in the case of phage and viral vectors may also be, and preferably are, introduced into cells as packaged or encapsidated virus by well known techniques for infection and transduction. Viral vectors may be replication competent or replication defective. In the latter case, viral propagation generally will occur only in complementing host cells.

Preferred among vectors, in certain respects, are those for expression of polynucleotides and polypeptides of the present invention. Generally, such vectors comprise cis-acting control regions effective for expression in a host operatively linked to the polynucleotide to be expressed. Appropriate trans-acting factors are either supplied by the host, supplied by a complementing vector or supplied by the vector itself upon introduction into the host.

In certain preferred embodiments, the vectors provide for specific expression. Such specific expression may be inducible expression or expression only in certain types of cells, or both inducible and cell-specific expression. Particularly preferred among inducible vectors are vectors that can be induced to express a protein by environmental factors that are easy to manipulate, such as temperature and nutrient additives. A variety of vectors suitable to this aspect of the invention, including constitutive and inducible expression vectors for use in prokaryotic and eukaryotic hosts, are well known and employed routinely by those of skill in the art.

The engineered host cells can be cultured in conventional nutrient media, which may be modified as appropriate for, inter alia, activating promoters, selecting transfoimants or amplifying genes. Culture conditions, such as temperature, pH and the like, previously used with the host cell selected for expression, generally will be suitable for expression of polypeptides of the present invention as will be apparent to those of skill in the art.

A great variety of expression vectors can be used to express a polypeptide of the invention. Such vectors include chromosomal, episomal and virus-derived vectors e.g., vectors derived from bacterial plasmids, bacteriophages, yeast episomes, yeast chromosomal elements, and viruses such as baculoviruses, papova viruses, SV40, vaccinia viruses, adenoviruses, fowl pox viruses, pseudorabies viruses and retroviruses, and vectors derived from combinations thereof, such as those derived from plasmid and bacteriophage genetic elements, cosmids and phagemids. Generally, any vector suitable to maintain, propagate or express polynucleotides to produce a polypeptide in a host may be used for expression in this regard.

The appropriate DNA sequence may be inserted into the vector by any of a variety of well-known and routine techniques. In general, a DNA sequence for expression is joined to an expression vector by cleaving the DNA sequence and the expression vector with one or more restriction endonucleases and then joining the restriction fragments together using T4 DNA ligase. Procedures for restriction and ligation that can be used to this end are well known and routine to those of skill. Suitable procedures in this regard, and for constructing expression vectors using alternative techniques, which also are well known and routine to those skilled in the art, are set forth in great detail in Sambrook et al.

The DNA sequence in the expression vector is operatively linked to appropriate expression control sequence(s), including, for instance, a promoter to direct mRNA transcription. Representatives of such promoters include, but are not limited to, the phage lambda PL promoter, the E. coli lac, trp and tac promoters, the SV40 early and late promoters and promoters of retroviral LTRs. Numerous other promoters useful in this aspect of the invention are also well known and may be routinely employed by those of skill in the manner illustrated by the discussion and the examples herein.

In general, expression constructs will contain sites for transcription initiation and termination, and, in the transcribed region, a ribosome binding site for translation. The coding portion of the mature transcripts expressed by the constructs will include a translation initiating AUG at the beginning and a termination codon appropriately positioned at the end of the polypeptide to be translated.

In addition, the constructs may contain control regions that regulate, as well as engender, expression. Generally, in accordance with many commonly practiced procedures, such regions will operate by controlling transcription. Examples include repressor binding sites and enhancers, among others.

Vectors for propagation and expression generally will include selectable markers. Selectable marker genes provide a phenotypic trait for selection of transformed host cells. Preferred markers include, but are not limited to, dihydrofolate reductase or neomycin resistance for eukaryotic cell culture, and tetracycline or ampicillin resistance genes for culturing E. coli and other bacteria. Such markers may also be suitable for amplification. Alternatively, the vectors may contain additional markers for this purpose.

The vector containing the appropriate nucleotide sequence as described elsewhere herein, as well as an appropriate promoter, and other appropriate control sequences, may be introduced into an appropriate host using a variety of well known techniques suitable for expression therein of a desired polypeptide. Representative examples of appropriate hosts include bacterial cells, such as E. coli, Streptomyces and Salmonella typhimurium cells; fungal cells, such as yeast cells; insect cells such as Drosophila S2 and Spodoptera Sf9 cells; animal cells such as CHO, COS and Bowes melanoma cells; and plant cells. Hosts of a great variety of expression constructs are well known, and those of skill will be enabled by the present disclosure to routinely select a host for expressing a polypeptide in accordance with this aspect of the present invention.

The present invention also comprises recombinant constructs, such as expression constructs, comprising one or more of the sequences described above. The constructs comprise a vector, such as a plasmid or viral vector, into which such a sequence of the invention has been inserted. The sequence may be inserted in a forward or reverse orientation. In certain preferred embodiments in this regard, the construct further comprises regulatory sequences, including, for example, a promoter, operably linked to the sequence. Large numbers of suitable vectors and promoters are known to those of skill in the art, and there are many commercially available vectors suitable for use in the present invention.

The following vectors, which are commercially available, are provided by way of example. Among vectors preferred for use in bacteria are pQE70, pQE60 and pQE-9, available from Qiagen; pBS vectors, Phagescript vectors, Bluescript vectors, pNH8A, pNH16a, pNH18A, pNH46A, available from Stratagene (La Jolla, Calif.); and ptrc99a, pKK223-3, pKK233-3, pDR540, pRIT5 available from Pharmacia (Uppsala, Sweden). Among preferred eukaryotic vectors are pWLNEO, pSV2CAT, pOG44, pXT1 and pSG available from Stratagene; and pSVK3, pBPV, pMSG and pSVL available from Pharmacia. These vectors are listed solely by way of illustration of the many commercially available and well known vectors that are available to those of skill in the art for use in accordance with this aspect of the present invention. It will be appreciated that any other plasmid or vector suitable for, for example, introduction, maintenance, propagation or expression of a polynucleotide or polypeptide of the invention in a host may be used in this aspect of the invention.

Promoter regions can be selected from any desired gene using vectors that contain a reporter transcription unit lacking a promoter region, such as a chloramphenicol acetyl transferase ("CAT") transcription unit, downstream of a restriction site or sites for introducing a candidate promoter fragment; i.e., a fragment that may contain a promoter. As is well known, introduction into the vector of a promoter-containing fragment at the restriction site upstream of the CAT gene engenders production of CAT activity, which can be detected by standard CAT assays. Vectors suitable to this end are well known and readily available. Two examples of such vectors include pKK232-8 and pCM7. Thus, promoters for expression of polynucleotides of the present invention include not only well known and readily available promoters, but also promoters that may be readily obtained by the foregoing technique, using a reporter gene.

Among known bacterial promoters suitable for expression of polynucleotides and polypeptides in accordance with the present invention are the E. coli lacI and lacZ promoters, the T3 and T7 promoters, the gpt promoter, the lambda PR, PL promoters and the trp promoter. Among known eukaryotic promoters suitable in this regard are the CMV immediate early promoter, the HSV thymidine kinase promoter, the early and late SV40 promoters, the promoters of retroviral LTRs, such as those of the Rous Sarcoma Virus("RSV"), and metallothionein promoters, such as the mouse metallothionein-I promoter.

Selection of appropriate vectors and promoters for expression in a host cell is a well known procedure and the requisite techniques for construction of expression vectors, introduction of the vector into the host and expression in the host are routine skills in the art.

The present invention also relates to host cells containing the above-described constructs. The host cell can be a higher eukaryotic cell, such as a mammalian cell, a lower eukaryotic cell, such as a yeast cell, or a prokaryotic cell, such as a bacterial cell.

Introduction of the construct into the host cell can be effected by calcium phosphate transfection, DEAE-dextran mediated transfection, cationic lipid-mediated transfection, electroporation, transduction, infection or other methods. Such methods are described in many standard laboratory manuals.

Constructs in host cells can be used in a conventional manner to produce the gene product encoded by the recombinant sequence. Alternatively, the polypeptides of the invention can be synthetically produced by conventional peptide synthesizers.

Mature proteins can be expressed in mammalian, yeast, bacteria, or other cells under the control of appropriate promoters. Cell-free translation systems can also be employed to produce such proteins using RNAs derived from the DNA constructs of the present invention. Appropriate cloning and expression vectors for use with prokaryotic and eukaryotic hosts are described by Sambrook et al.

Generally, recombinant expression vectors will include origins of replication, a promoter derived from a highly-expressed gene to direct transcription of a downstream structural sequence, and a selectable marker to permit isolation of vector containing cells following exposure to the vector. Among suitable promoters are those derived from the genes that encode glycolytic enzymes such as 3-phosphoglycerate kinase ("PGK"), a-factor, acid phosphatase, and heat shock proteins, among others. Selectable markers include the ampicillin resistance gene of *E. coli* and the trpl gene of *S. cerevisiae*.

Transcription of DNA encoding the polypeptides of the present invention by higher eukaryotes may be increased by inserting an enhancer sequence into the vector. Enhancers are cis-acting elements of DNA, usually from about 10 to 300 bp, that act to increase transcriptional activity of a promoter in a given host cell-type. Examples of enhancers include the SV40 enhancer, which is located on the late side of the replication origin at bp 100 to 270, the cytomegalovirus early promoter enhancer, the polyoma enhancer on the late side of the replication origin, and adenovirus enhancers.

A polynucleotide of the invention encoding the heterologous structural sequence of a polypeptide of the invention generally will be inserted into the vector using standard techniques so that it is operably linked to the promoter for expression. The polynucleotide will be positioned so that the transcription start site is located appropriately 5' to a ribosome binding site. The ribosome binding site will be 5' to the AUG that initiates translation of the polypeptide to be expressed. Generally, there will be no other open reading frames that begin with an initiation codon, usually AUG, and lie between the ribosome binding site and the initiation codon. Also, generally, there will be a translation stop codon at the end of the polypeptide and a polyadenylation signal and transcription termination signal appropriately disposed at the 3' end of the transcribed region.

Appropriate secretion signals may be incorporated into the expressed polypeptide for secretion of the translated protein into the lumen of the endoplasmic reticulum, the periplasmic space or the extracellular environment,. The signals may be endogenous to the polypeptide or heterologous.

The polypeptide may be expressed in a modified form, such as a fusion protein, and may include not only secretion signals but also additional heterologous functional regions. Thus, for example, a region of additional amino acids, particularly charged amino acids, may be added to the N-terninus of the polypeptide to improve stability and persistence in the host cell during purification or subsequent handling and storage. A region may also be added to the polypeptide to facilitate purification. Such regions may be removed prior to final preparation of the polypeptide. The addition of peptide moieties to polypeptides to engender secretion or excretion, to improve stability and to facilitate purification, among others, is well known, utilizing techniques routine to those of skill in the art.

Suitable prokaryotic hosts for propagation, maintenance or expression of polynucleotides and polypeptides in accordance with the invention include *Escherichia coli, Bacillus subtilis* and *Salmonella typhimurium*. Various species of Pseudomonas, Streptomyces, and Staphylococcus are also suitable hosts in this regard. Moreover, many other hosts also known to those of skill may be employed in this regard.

As a representative but non-limiting example, useful expression vectors for bacterial use can comprise a selectable marker and bacterial origin of replication derived from commercially available plasmids comprising genetic elements of the well known cloning vector pBR322 (ATCC 37017). Such commercial vectors include, for example, pKK223-3 (Pharmacia Fine Chemicals, Uppsala, Sweden) and GEM1 (Promega Biotec, Madison, Wis., USA). In these vectors, the pBR322 "backbone" sections are combined with an appropriate promoter and the structural sequence to be expressed.

Following transformation of a suitable host strain, the host strain is grown to an appropriate cell density. Where the selected promoter is inducible, it is induced by appropriate means (e.g., temperature shift or exposure to chemical inducer) and cells are cultured for an additional period. Cells typically then are harvested by centrifugation, disrupted by physical or chemical means, and the resulting crude extract retained for further purification.

Microbial cells employed in expression of proteins can be disrupted by any convenient method, including freeze-thaw cycling, sonication, mechanical disruption, or use of cell lysing agents. Such methods are well known to those skilled in the art.

Various mammalian cell culture systems can be employed for expression, as well. Examples of mammalian expression systems include, but are not limited to, the C127, 3T3, CHO, HeLa, human kidney 293 and BHK cell lines, along with the COS-7 line of monkey kidney fibroblasts, described by Gluzman et al, *Cell*, 1981, 23:175.

Mammalian expression vectors will comprise an origin of replication, a suitable promoter and enhancer, and any necessary ribosome binding sites, polyadenylation sites, splice donor and acceptor sites, transcriptional termination sequences, and 5' flanking non-transcribed sequences that are necessary for expression. In certain preferred embodiments, DNA sequences derived from the SV40 splice sites and the SV40 polyadenylation sites are used for required non-transcribed genetic elements.

The HLTEX11 polypeptide can be recovered and purified from recombinant cell cultures by well-known methods including ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Most preferably, high performance liquid chromatography ("HPLC") is employed for purification. Well known techniques for refolding proteins may be employed to regenerate active conformation when the polypeptide is denatured during isolation and or purification.

Polypeptides of the present invention include naturally purified polypeptides, polypeptides produced by chemical synthetic procedures, and polypeptides produced by recombinant techniques from a prokaryotic or eukaryotic host, including, for example, bacterial, yeast, higher plant, insect and mammalian cells. Depending upon the host employed in a recombinant production procedure, the polypeptides of the present invention may be glycosylated or non-glycosylated. In addition, polypeptides of the invention may include an initial modified methionine residue, in some cases as a result of host-mediated processes.

HLTEX11 polynucleotides and polypeptides may be used in accordance with the present invention for a variety of applications, particularly those that make use of the chemical and biological properties of HLTEX11. Additional applications relate to diagnosis and to treatment of disorders of cells, tissues and organisms. These aspects of the invention are illustrated further by the following discussion.

Polynucleotide assays

This invention is also related to the use of the HLTEX11 polynucleotides to detect complementary polynucleotides such as, for example, as a diagnostic reagent. Detection of a mutated form of HLTEX11 associated with a dysfunction will provide a diagnostic tool that can add or define a diagnosis of a disease or susceptibility to a disease which results from under-expression, over-expression or altered expression of HLTEX11. Individuals carrying mutations in the human HLTEX11 gene may be detected at the DNA level by a variety of techniques. Nucleic acids for diagnosis may be obtained from a patient's cells, such as from blood, urine, saliva, tissue biopsy and autopsy material. The genomic DNA may be used directly for detection or may be amplified enzymatically by using PCR prior to analysis. Saiki et al., Nature, 1986 324: 163–166. For example, PCR primers complementary to the nucleic acid encoding HLTEX11 can be used to identify and analyze HLTEX11 expression and mutations. For example, deletions and insertions can be detected by a change in size of the amplified product in comparison to the normal genotype. Point mutations can be identified by hybridizing amplified DNA to radiolabeled HLTEX11 RNA or alternatively, radiolabeled HLTEX11 antisense DNA sequences. Perfectly matched sequences can be distinguished from mismatched duplexes by RNase A digestion or by differences in melting temperatures.

Sequence differences between a reference gene and genes having mutations may also be revealed by direct DNA sequencing. In addition, cloned DNA segments may be employed as probes to detect specific DNA segments. The sensitivity of such methods can be greatly enhanced by appropriate use of PCR or another amplification method. For example, a sequencing primer is used with a double-stranded PCR product or a single-stranded template molecule generated by modified PCR. The sequence determination is performed by conventional procedures with radiolabeled nucleotide or by automatic sequencing procedures with fluorescent-tags.

Genetic testing based on DNA sequence differences may be achieved by detection of alterations in electrophoretic mobility of DNA fragments in gels, with or without denaturing agents. Small sequence deletions and insertions can be visualized by high resolution gel electrophoresis. DNA fragments of different sequences may be distinguished on denaturing formamide gradient gels in which the mobilities of different DNA fragments are retarded in the gel at different positions according to their specific melting or partial melting temperatures (see, e.g., Myers et al., Science, 1985, 230: 1242).

Sequence changes at specific locations also may be revealed by nuclease protection assays, such as RNase and S1 protection or the chemical cleavage method (e.g., Cotton et al., Proc. Natl Acad. Sci., USA, 1985, 85: 4397–4401).

Thus, the detection of a specific DNA sequence may be achieved by methods such as hybridization, RNase protection, chemical cleavage, direct DNA sequencing or the use of restriction enzymes, (e.g., restriction fragment length polymorphisms ("RFLP") and Southern blotting of genomic DNA.

In addition to more conventional gel-electrophoresis and DNA sequencing, mutations can also be detected by in situ analysis.

In accordance with a further aspect of the invention, there is provided a process for determining atherosclerosis, restenosis, stroke, inflammatory disease, and infections, such as viral infections, particularly HIV-1 or a susceptibility to these diseases. A mutation in the HLTEX11 gene can be indicative of a susceptibility to atherosclerosis, restenosis, stroke, inflammatory disease, and infections, such as viral infections, particularly HIV-1, and the nucleic acid sequences described above may be employed in an assay for ascertaining such susceptibility. Thus, the assay may be employed, for example, to determine a mutation in a human HLTEX11 gene as herein described, such as a deletion, truncation, insertion, frame shift, etc., with such mutation being indicative of a susceptibility to atherosclerosis, restenosis, stroke, inflammatory disease, and infections, such as viral infections, particularly HIV-1.

A mutation may be ascertained for example, by a DNA sequencing assay. Tissue samples, including but not limited to blood samples are obtained from a human patient. The samples are processed by methods known in the art to capture the RNA. First strand cDNA is synthesized from the RNA samples by adding an oligonucleotide primer consisting of polythymidine residues which hybridize to the polyadenosine stretch present on the mRNA's. Reverse transcriptase and deoxynucleotides are added to allow synthesis of the first strand cDNA. Primer sequences are synthesized based on the DNA sequence of the DNA repair protein of the invention. The primer sequence is generally comprised of at least 15 consecutive bases, and may contain at least 30 or even 50 consecutive bases.

RT-PCR can also be used to detect mutations. It is particularly preferred to used RT-PCR in conjunction with automated detection systems, such as, for example, GeneScan. As an example, PCR primers complementary to the nucleic acid encoding HLTEX11 can be used to identify and analyze mutations. Examples of representative primers include GeneTrapper Primers or PCR sense primers:

5' GGA TGG TGT TCA TGT GTG CTG 3' (SEQ ID NO:3);

5' CTT CAT CTG CTT CAC TCC CT 3' (SEQ ID NO:4); and the PCR antisense primer:

5' CAC AGA ACT GCC ATG GCG GG 3' (SEQ ID NO:5).

Deletions and insertions can be detected by a change in size of the amplified product in comparison to the normal genotype. Point mutations can be identified by hybridizing amplified DNA to radiolabeled RNA or, alternatively, radiolabeled antisense DNA sequences. Perfectly matched sequences can be distinguished from mismatched duplexes by RNase A digestion or by differences in melting temperatures.

These primers may also be used for amplifying HLTEX11 cDNA isolated from a sample derived from a patient. The invention also relates to primers having 1, 2, 3 or 4 nucleotides removed from the 5' and/or the 3' end. Such primers may be used to amplify the gene isolated from the patient so that the gene may then be subjected to various techniques for elucidation of the DNA sequence such as gel-electrophoresis and DNA sequencing. In this way, mutations in the DNA sequence may be diagnosed.

Mutations can also be detected by in situ analysis.

Chromosome assays

The sequences of the present invention are also valuable for chromosome identification. The sequence is specifically targeted to and can hybridize with a particular location on an individual human chromosome. Moreover, there is a current need for identifying particular sites on the chromosome. Few chromosome marking reagents based on actual sequence data (repeat polymorphisms) are presently available for marking chromosomal location. The mapping of DNAs to chromosomes according to the present invention is an important first step in correlating those sequences with gene associated disease.

Briefly, sequences can be mapped to chromosomes by preparing PCR primers (preferably 15–25 bp) from the cDNA. Computer analysis of the 3' untranslated region is used to rapidly select primers that do not span more than one exon in the genomic DNA, because primers that span more than one exon could complicate the amplification process. These primers are then used for PCR screening of somatic cell hybrids containing individual human chromosomes. Only those hybrids containing the human gene corresponding to the primer will yield an amplified fragment.

PCR mapping of somatic cell hybrids is a rapid procedure for assigning a particular DNA to a particular chromosome. Using the present invention with the same oligonucleotide primers, sublocalization can be achieved with panels of fragments from specific chromosomes or pools of large genomic clones in an analogous manner. Other mapping strategies that can be used similarly to map to the chromosome include in situ hybridization, prescreening with labeled flow-sorted chromosomes and preselection by hybridization to construct chromosome specific-cDNA libraries.

Fluorescence in situ hybridization (FISH) of a cDNA clone to a metaphase chromosomal spread can be used to provide a precise chromosomal location in one step. This technique can be used with cDNAs as short as 50 to 60 bases. For a review of this technique, see Verma et al., HUMAN CHROMOSOMES: A MANUAL OF BASIC TECHNIQUES, PERGAMON PRESS, NEW YORK, 1988.

As an example of how this technique is performed, HLTEX11 DNA is digested and purified with QIAEX II DNA purification kit (Qiagen, Inc., Chatsworth, Calif.) and ligated to Super Cos1 cosmid vector (Stratagene, La Jolla, Calif.). DNA is purified using Qiagen Plasmid Purification Kit (Qiagen Inc., Chatsworth, Calif.) and 1 mg is labeled by nick translation in the presence of Biotin-dATP using BioNick Labeling Kit (GibcoBRL, Life Technologies Inc., Gaithersburg, Md.). Biotinylation is detected with GENE-TECT Detection System (Clontech Laboratories, Inc. Palo Alto, Calif.). In situ hybridization is performed on slides using ONCOR Light Hybridization Kit (Oncor, Gaithersberg, Md.) to detect single copy sequences on metaphase chromosomes. Peripheral blood of normal donors is cultured for three days in RPMI 1640 supplemented with 20% FCS, 3% PHA and penicillin/streptomycin, synchronized with $10^{-7}$M methotrexate for 17 hours, and washed twice with unsupplemented RPMI. Cells are then incubated with $10^{-3}$M thymidine for 7 hours. The cells are arrested in metaphase after a 20 minute incubation with colcemid (0.5 $\mu$g/ml) followed by hypotonic lysis in 75 mM KCl for 15 minutes at 37° C. Cell pellets are then spun out and fixed in Carnoy's fixative (3:1 methanol/acetic acid).

Metaphase spreads are prepared by adding a drop of the suspension onto slides and air drying the suspension. Hybridization is performed by adding 100 ng of probe suspended in 10 ml of hybridization mix (50% formamide, 2×SSC, 1% dextran sulfate) with blocking human placental DNA (1 $\mu$g/ml). Probe mixture is denatured for 10 minutes in a 70° C. water bath and incubated for 1 hour at 37° C., before placement on a prewarmed (37° C.) slide, previously denatured in 70% formamide/2×SSC at 70° C., dehydrated in ethanol series, and chilled to 4° C. Slides are then incubated for 16 hours at 37° C. in a humidified chamber and washed in 50% formamide/2×SSC for 10 minutes at 41° C. and 2×SSC for 7 minutes at 37° C. Hybridization probe is detected by incubation of the slides with FITC-Avidin (Oncor, hiGaithersberg, Md.), according to the manufacturer's protocol. Chromosomes are counterstained with propridium iodine suspended in mounting medium. Slides are visualized using a Leitz ORTHOPLAN 2-epifluorescence microscope. Five computer images are taken using a Imagenetics Computer and MacIntosh printer.

Once a sequence has been mapped to a precise chromosomal location, the physical position of the sequence on the chromosome can be correlated with genetic map data. Such data are found, for example, in V. McKusick, Mendelian Inheritance in Man (available on line through Johns Hopkins University Welch Medical Library). The relationship between genes and diseases that have been mapped to the same chromosomal region are then identified through linkage analysis (coinheritance of physically adjacent genes).

It is then necessary to determine the differences in the cDNA or genomic sequence between affected and unaffected individuals. If a mutation is observed in some or all of the affected individuals, but not in any normal individuals, then the mutation is likely to be the causative agent of the disease.

With current resolution of physical mapping and genetic mapping techniques, a cDNA precisely localized to a chromosomal region associated with the disease could be one of between 50 and 500 potential causative genes assuming 1 megabase mapping resolution and one gene per 20 kb.

Polypeptide assays

The present invention also relates to diagnostic assays for detecting levels of HLTEX11 protein in cells and tissues. Such assays may be quantitative or qualitative, Thus, for instance, a diagnostic assay in accordance with the invention for detecting over-expression of HLTEX11 protein compared to normal control tissue samples may be used to detect the presence of a disease or disorder such as atherosclerosis, restenosis, stroke, inflammatory disease, or infections, such as viral infections, particularly HIV-1, among others. Assay techniques that can be used to determine levels of a protein, such as an HLTEX11 protein of the present invention, in a sample derived from a host are well-known to those of skill in the art. Such assay methods include radioimmunoassays, competitive-binding assays, Western Blot analysis and enzyme linked immunosorbent assays (ELISAs). Among these, ELISAs are frequently preferred. An ELISA assay initially comprises preparing an antibody specific to HLTEX11, preferably a monoclonal antibody. In addition a reporter antibody generally is prepared which binds to the monoclonal antibody. The reporter antibody is attached to a detectable reagent such as a radioactive, fluorescent or enzymatic reagent, in this example, horseradish peroxidase enzyme.

To carry out an ELISA, a sample is removed from a host and incubated on a solid support, e.g. a polystyrene dish, that binds the proteins in the sample. Any free protein binding sites on the dish are then covered by incubating with a non-specific protein such as bovine serum albumin. The monoclonal antibody is then incubated in the dish during which time the monoclonal antibodies attach to any HLTEX11 proteins attached to the polystyrene dish. Unbound monoclonal antibody is washed out with buffer. The reporter antibody linked to horseradish peroxidase is placed in the dish resulting in binding of the reporter antibody to any monoclonal antibody bound to HLTEX11. Unattached reporter antibody is then washed out. Reagents for peroxidase activity, including a colorimetric substrate are then added to the dish. Immobilized peroxidase, linked to HLTEX11 through the primary and secondary antibodies, produces a colored reaction product. The amount of color developed in a given time period indicates the amount of HLTEX11 protein present in the sample. Quantitative results typically are obtained by reference to a standard curve.

A competition assay may also be employed wherein antibodies specific to HLTEX11 attached to a solid support and labeled HLTEX11 and a sample derived from the host are passed over the solid support. The amount of detected label attached to the solid support can be correlated to a quantity of HLTEX11 in the sample.

Antibodies

The polypeptides, their fragments or other derivatives, or analogs thereof, or cells expressing them can also be used as immunogens to produce antibodies thereto. These antibodies can be, for example, polyclonal or monoclonal antibodies. The present invention also includes chimeric, single chain, and humanized antibodies, as well as Fab fragments, or the product of a Fab expression library. Various procedures known in the art may be used for the production of such antibodies and fragments.

Antibodies generated against polypeptides corresponding to a sequence of the present invention can be obtained by various means well known to those of skill in the art. For example, in one embodiment, the polypeptide is directly injected into an animal, preferably a nonhuman. The antibody so obtained will then bind the polypeptide itself. In this embodiment, even a sequence encoding only a fragment of the polypeptide can be used to generate antibodies binding the whole native polypeptide. Such antibodies can then be used to isolate the polypeptide from tissues expressing that polypeptide.

For preparation of monoclonal antibodies, any technique which provides antibodies produced by continuous cell cultures can be used. Examples include the hybridoma technique (Kohler, G. and Milstein, C., *Nature*, 1975, 256:495–497), the trioma technique, the human B-cell hybridoma technique (Kozbor et al., *Immunology Today*, 1983, 4:72) and the EBV-hybridoma technique (Cole et al., MONOCLONAL ANTIBODIES AND CANCER THERAPY, pages 77–96, Alan R. Liss, Inc., 1985).

Techniques described for the production of single chain antibodies (U.S. Pat. No. 4,946,778) can also be adapted to produce single chain antibodies to immunogenic polypeptide products of this invention. Also, transgenic mice, or other organisms including other mammals, may be used to express humanized antibodies to immunogenic polypeptide products of this invention.

The above-described antibodies may be employed to isolate or identify clones expressing the polypeptide or to purify the polypeptide of the present invention by attachment of the antibody to a solid support for isolation and/or purification by affity chromatography.

In addition, antibodies against HLTEX11 may be employed to inhibit atherosclerosis, restenosis, stroke and inflammation (chronic and acute)., among others. Antibodies which inhibit HLTEX11 are also useful in inhibiting virus binding and viral infection, particularly HIV-1 binding and infection.

HLTEX11 binding molecules and assays

This invention also provides a method for identification of molecules, such as binding molecules, that bind HLTEX11. Genes encoding proteins that bind HLTEX11, such as binding molecule proteins, can be identified by numerous methods known to those of skill in the art including ligand panning using, for example, PAF, and FACS sorting. Such methods are described in many laboratory manuals such as Coligan et al., CURRENT PROTOCOLS IN IMMUNOLOGY 1(2): Chapter 5 (1991).

For example, expression cloning may be employed for this purpose. In this method, polyadenylated RNA is prepared from a cell responsive to HLTEX11. A cDNA library is created from this RNA. The library is then divided into pools and the pools transfected individually into cells that are not responsive to HLTEX11. The transfected cells are then exposed to labeled HLTEX11. HLTEX11 can be labeled by a variety of well-known techniques including, but not limited to, standard methods of radio-iodination or inclusion of a recognition site for a site-specific protein kinase. Following exposure, the cells are fixed and binding of HLTEX11 is determined. These procedures can be conveniently carried out on glass slides.

Pools of cDNA that produced HLTEX11-binding cells as identified as positives. Sub-pools are then prepared from these positives, transfected into host cells and screened as described above. Using an iterative sub-pooling and re-screening process, one or more single clones that encode the putative binding molecule, such as a binding molecule, can be isolated.

Alternatively, a labeled ligand, such as PAF, can be photoaffinity-linked to a cell extract, such as a membrane or a membrane extract, prepared from cells that express a molecule to which the ligand binds. Cross-linked material is resolved by polyacrylamide gel electrophoresis ("PAGE") and exposed to X-ray film. The labeled complex containing the ligand-receptor can be excised, resolved into peptide fragments, and subjected to protein microsequencing. The amino acid sequence obtained from microsequencing can be used to design unique or degenerate oligonucleotide probes to screen cDNA libraries to identify genes encoding the putative receptor molecule.

Polypeptides of the invention can also be used to assess HLTEX11 binding capacity of HLTEX11 binding molecules in cells or in cell-free preparations.

Agonists and antagonists—assays and molecules

HLTEX11 of the present invention may also be employed in a process for screening for compounds which act as agonists or antagonists of the receptor polypeptide of the present invention. An agonist is a compound which increases the natural biological functions of HLTEX11 or which functions in a manner similar to HLTEX11, while antagonists decrease or eliminate such functions. The invention also provides a method of screening compounds to identify those which enhance or block the action of HLTEX11 on cells, such as its interaction with HLTEX11-binding molecules such as receptor molecules.

In general, such screening procedures involve providing appropriate cells which express the receptor polypeptide of the present invention on the surface thereof. Such cells include cells from mammals, yeast, Drosophila or E. Coli.

In one embodiment, a polynucleotide encoding the receptor of the present invention is employed to transfect cells to thereby express the HLTEX11. The expressed receptor is then contacted with a test compound to observe binding, stimulation or inhibition of a functional response.

One such screening procedure involves the use of melanophores which are transfected to express the G-Protein Coupled Receptor HLTEX11 of the present invention. Such a screening technique is described in PCT WO92/01810 published Feb. 6, 1992. In this method, a compound which inhibits activation of the receptor polypeptide of the present invention can be determined by contacting the melanophore cells which encode the receptor with both a receptor ligand, such as PAF, and a compound to be screened. Inhibition of the signal generated by ligand indicates that a compound is a potential antagonist for the receptor, i.e., inhibits activation of the receptor. The screen may also be employed for determining a compound which activates the receptor by contacting such cells with compounds to be screened and determining whether such compound generates a signal, i.e., activates the receptor.

Other screening techniques include the use of cells which express HLTEX11, for example, transfected CHO cells, in a system which measures a signal response such as extracellular pH changes caused by receptor activation. In this method, compounds may be contacted with a cell which expresses the receptor polypeptide of the present invention and a second messenger response, e.g. signal transduction or pH changes, may be measured to determine whether the potential compound activates or inhibits the receptor.

Another such screening technique involves introducing RNA encoding HLTEX11 into Xenopus oocytes to transiently express the receptor. The receptor oocytes may then be contacted with a receptor ligand, such as PAF, and a compound to be screened, followed by detection of inhibition or activation of a signal, e.g., proton, and other ion signal, but particularly calcium ion signal, in screening for compounds which are thought to inhibit activation of the receptor.

Another screening technique involves expressing HLTEX11 wherein the receptor is linked to, e.g., phospholipase C or D or other proteins. As representative examples of such cells, there may be mentioned endothelial cells, smooth muscle cells, embryonic kidney cells, etc. The screening may be accomplished as hereinabove described by detecting activation of the receptor or inhibition of activation of the receptor from a second signal, such as for example, phospholipase or other activated/expressed protein.

Another method involves screening for compounds which inhibit activation of the receptor polypeptide of the present invention antagonists by determining inhibition of binding of labeled ligand, such as, for example PAF, to cells which have the receptor on the surface thereof. Such a method involves transfecting a eukaryotic cell with DNA encoding HLTEX11 such that the cell expresses the receptor on its surface and contacting the cell with a compound in the presence of a labeled form of a known ligand such as PAF. Ligand can be labeled, e.g., by radioactivity. The amount of labeled ligand bound to the receptors is measured, e.g., by scintillation counting. If the compound binds to the receptor as determined by a reduction of labeled ligand which binds to the receptors, the binding of labeled ligand to the receptor is inhibited.

Alternatively, a cellular compartment, such as a membrane or a preparation thereof, such as a membrane-preparation, may be prepared from a cell that expresses a molecule that binds HLTEX11, such as a molecule of a signaling or regulatory pathway modulated by HLTEX11. The preparation is incubated with labeled HLTEX11 in the absence or the presence of a candidate molecule which may be a HLTEX11 agonist or antagonist. The ability of the candidate molecule to bind the binding molecule is reflected in decreased binding of the labeled ligand. Molecules which bind gratuitously, i.e., without inducing the effects of HLTEX11 on binding the HLTEX11 binding molecule, are most likely to be good antagonists. Molecules that bind well and elicit effects that are the same as or closely related to HLTEX11 are agonists.

HLTEX11-like effects of potential agonists and antagonists may also be measured, for instance, by determining activity of a second messenger system following interaction of the candidate molecule with a cell or appropriate cell preparation, and comparing the effect with that of HLTEX11 or molecules that elicit the same effects as HLTEX11. Second messenger systems that may be useful in this regard include but are not limited to AMP guanylate cyclase, ion channel or phosphoinositide hydrolysis second messenger systems.

Another example of an assay for HLTEX11 antagonists is a competitive assay that combines HLTEX11 and a potential antagonist with membrane-bound HLTEX11 receptor molecules or recombinant HLTEX11 receptor molecules under appropriate conditions for a competitive inhibition assay. HLTEX11 can be labeled, such as by radioactivity, such that the number of HLTEX11 molecules bound to a receptor molecule can be determined accurately to assess the effectiveness of the potential antagonist.

HLTEX11 are ubiquitous in the mammalian host and are responsible for many biological functions, including many pathologies. Accordingly, it is desirous to find compounds and drugs which stimulate HLTEX11 on the one hand and which can inhibit the function of HLTEX11 on the other hand.

For example, compounds which activate HLTEX11 may be employed for therapeutic purposes, such as the treatment of cancer and infectious disease.

In general, compounds which inhibit activation of HLTEX11 may be employed for a variety of therapeutic purposes, for example, for the treatment of stroke, atherosclerosis, restenosis and inflammation (chronic and acute). Compounds which inhibit HLTEX11 are also useful in inhibiting virus binding and viral infection, particularly HIV-1 binding and infection.

Antibodies against HLTEX11 may be used to antagonize the activity of HLTEX11. Antibodies include anti-idiotypic antibodies which recognize unique determinants generally associated with the antigen-binding site of an antibody. Potential antagonist compounds also include proteins which are closely related to a ligand of HLTEX11, i.e. a fragment of a ligand, which have lost biological function and when binding to HLTEX11, elicit no response. For example, fragments of PAF are believed to be useful as antagonists of HLTEX11.

An antisense construct prepared through the use of antisense technology, may also be used to control gene expression through triple-helix formation or antisense DNA or RNA, both of which methods are based on binding of a polynucleotide to DNA or RNA. For example, the 5' coding portion of the polynucleotide sequence, which encodes for the mature polypeptides of the present invention, is used to design an antisense RNA oligonucleotide of from about 10 to 40 base pairs in length. A DNA oligonucleotide is designed to be complementary to a region of the gene involved in transcription (triple helix -see Lee et al., *Nucl. Acids Res.*, 1979, 6:3073; Cooney et al, *Science*, 1988, 241:456; and Dervan et al., *Science*, 1991, 251:1360), thereby preventing transcription and the production of HLTEX11. The antisense RNA oligonucleotide hybridizes to the mRNA in vivo and blocks translation of mRNA molecules into HLTEX11 (antisense—Okano, *J Neurochem.*, 1991, 56:560 (1991); Oligodeoxynucleotides as Antisense Inhibitors of Gene Expression, CRC Press, Boca Raton, FL(1988)). The oligonucleotides described above can also be delivered to cells such that the antisense RNA or DNA may be expressed in vivo to inhibit production of HLTEX11.

A small molecule which binds to HLTEX11, making it inaccessible to ligands such that normal biological activity is prevented, for example small peptides or peptide-like molecules, may also be used to inhibit activation of the receptor polypeptide of the present invention.

A soluble form of HLTEX11, e.g. a fragment of the receptors, may be used to inhibit activation of the receptor by binding to a ligand to a polypeptide of the present invention and preventing ligand from interacting with membrane bound HLTEX11.

This invention additionally provides a method of treating an abnormal condition related to an excess of HLTEX11 activity which comprises administering to a subject the inhibitor compounds as hereinabove described along with a pharmaceutically acceptable carrier in an amount effective to inhibit activation by blocking binding of ligands to HLTEX11, or by inhibiting a second signal, and thereby alleviating the abnormal conditions.

The invention also provides a method of treating abnormal conditions related to an under-expression of HLTEX11 activity which comprises administering to a subject a therapeutically effective amount of a compound which activates the receptor polypeptide of the present invention as described above in combination with a pharmaceutically acceptable carrier, to thereby alleviate the abnormal conditions.

The soluble form of HLTEX11, and compounds which activate or inhibit such receptor, may be employed in combination with a suitable pharmaceutical carrier. Such compositions comprise a therapeutically effective amount of the polypeptide or compound, and a pharmaceutically acceptable carrier or excipient. Such a carrier includes but is not limited to saline, buffered saline, dextrose, water, glycerol, ethanol, and combinations thereof. The formulation should suit the mode of administration.

Compositions and Kits

The invention also relates to compositions comprising the polynucleotide or the polypeptides discussed above or the agonists or antagonists. Thus, the polypeptides of the present invention may be employed in combination with a non-sterile or sterile carrier or carriers for use with cells, tissues or organisms, such as a pharmaceutical carrier suitable for administration to a subject. Such compositions comprise, for instance, a media additive or a therapeutically effective amount of a polypeptide of the invention and a pharmaceutically acceptable carrier or excipient. Such carriers may include, but are not limited to, saline, buffered saline, dextrose, water, glycerol, ethanol and combinations thereof. The formulation should suit the mode of administration.

The invention further relates to pharmaceutical packs and kits comprising one or more containers filled with one or more of the ingredients of the aforementioned compositions of the invention. Associated with such container(s) can be a notice in the form prescribed by a governmental agency regulating the manufacture, use or sale of pharmaceuticals or biological products, reflecting approval by the agency of the manufacture, use or sale of the product for human administration.

Administration

Polypeptides and other compounds of the present invention may be employed alone or in conjunction with other compounds, such as therapeutic compounds.

The pharmaceutical compositions may be administered in any effective, convenient manner including, for instance, administration by topical, oral, anal, vaginal, intravenous, intraperitoneal, intramuscular, subcutaneous, intranasal or intradermal routes among others.

The pharmaceutical compositions generally are administered in an amount effective for treatment or prophylaxis of a specific indication or indications. In general, the compositions are administered in an amount of at least about 10 μg/kg body weight. In most cases they will be administered in an amount not in excess of about 8 mg/kg body weight per day. Preferably, in most cases, dose is from about 10 μg/kg to about 1 mg/kg body weight, daily. It will be appreciated that optimum dosage will be determined by standard methods for each treatment modality and indication, taking into account the indication, its severity, route of administration, complicating conditions and the like.

Gene therapy

The HLTEX11 polynucleotides, polypeptides, agonists and antagonists that are polypeptides may be employed in accordance with the present invention by expression of such polypeptides in treatment modalities often referred to as "gene therapy."

Thus, for example, cells from a patient may be engineered with a polynucleotide, such as a DNA or RNA, to encode a polypeptide ex vivo. The engineered cells can then be provided to a patient to be treated with the polypeptide. In this embodiment, cells may be engineered ex vivo, for example, by the use of a retroviral plasmid vector containing RNA encoding a polypeptide of the present invention. Such methods are well-known in the art and their use in the present invention will be apparent from the teachings herein.

Similarly, cells may be engineered in vivo for expression of a polypeptide in vivo by procedures known in the art. For example, a polynucleotide of the invention may be engineered for expression in a replication defective retroviral vector, as discussed above. The retroviral expression construct may then be isolated and introduced into a packaging cell transduced with a retroviral plasmid vector containing RNA encoding a polypeptide of the present invention such that the packaging cell now produces infectious viral particles containing the gene of interest. These producer cells may be administered to a patient for engineering cells in vivo and expression of the polypeptide in vivo. These and other methods for administering a polypeptide of the present invention should be apparent to those skilled in the art from the teachings of the present invention.

Retroviruses from which the retroviral plasmid vectors herein above mentioned may be derived include, but are not limited to, Moloney Murine Leukemia Virus, Spleen Necrosis Virus, Rous Sarcoma Virus, Harvey Sarcoma Virus, Avian Leukosis Virus, Gibbon Ape Leukemia Virus, Human Immunodeficiency Virus, Adenovirus, Myeloproliferative Sarcoma Virus, and Mammary Tumor Virus. In a preferred embodiment, the retroviral plasmid vector is derived from Moloney Murine Leukemia Virus.

Such vectors will include one or more promoters for expressing the polypeptide. Suitable promoters which may be employed include, but are not limited to, the retroviral LTR; the SV40 promoter; and the human cytomegalovirus (CMV) promoter described in Miller et al., *Biotechniques*, 1989, 7:980–990. Cellular promoters such as eukaryotic cellular promoters including, but not limited to, the histone, RNA polymerase III, and β-actin promoters can also be used. Additional viral promoters which may be employed include, but are not limited to, adenovirus promoters, thymidine kinase (TK) promoters, and B19 parvovirus promoters. The selection of a suitable promoter will be apparent to those skilled in the art from the teachings contained herein.

The nucleic acid sequence encoding the polypeptide of the present invention will be placed under the control of a suitable promoter. Suitable promoters which may be employed include, but are not limited to, adenoviral promoters, such as the adenoviral major late promoter; or heterologous promoters, such as the cytomegalovirus (CMV) promoter; the respiratory syncytial virus (RSV) promoter; inducible promoters, such as the MMT promoter, the metallothionein promoter; heat shock promoters; the albumin promoter; the ApoAI promoter; human globin promoters; viral thymidine kinase promoters, such as the Herpes Simplex thymidine kinase promoter; retroviral LTRs (including the modified retroviral LTRs herein above described); the β-actin promoter; and human growth hormone promoters. The promoter may also be the native promoter which controls the gene encoding the polypeptide.

The retroviral plasmid vector is employed to transduce packaging cell lines to form producer cell lines. Examples of packaging cells which may be transfected include, but are not limited to, the PE501, PA317, Y-2, Y-AM, PA12, T19-14X, VT-19-17-H2, YCRE, YCRIP, GP+E-86, GP+envAm12, and DAN cell lines as described in Miller, A., *Human Gene Therapy*, 1990, 1:5–14. The vector may be transduced into the packaging cells through any means known in the art. Such means include, but are not limited to, electroporation, the use of liposomes, and CaPO$_4$ precipitation. In one alternative, the retroviral plasmid vector may be encapsulated into a liposome, or coupled to a lipid, and then administered to a host.

The producer cell line will generate infectious retroviral vector particles, which include the nucleic acid sequence(s) encoding the polypeptides. Such retroviral vector particles may then be employed to transduce eukaryotic cells, either in vitro or in vivo. The transduced eukaryotic cells will express the nucleic acid sequence(s) encoding the polypeptide. Eukaryotic cells which may be transduced include, but are not limited to, embryonic stem cells, embryonic carcinoma cells, as well as hematopoietic stem cells, hepatocytes, fibroblasts, myoblasts, keratinocytes, endothelial cells, and bronchial epithelial cells.

EXAMPLES

The present invention is further described by the following examples. The examples are provided solely to illustrate the invention by reference to specific embodiments. These exemplifications, while illustrating certain specific aspects of the invention, do not portray the limitations or circumscribe the scope of the disclosed invention.

Certain terms used herein are explained in the foregoing glossary.

All examples are carried out using standard techniques, which are well known and routine to those of skill in the art, except where otherwise described in detail. Routine molecular biology techniques of the following examples can be carried out as described in standard laboratory manuals, such as Sambrook et al.

All parts or amounts set out in the following examples are by weight, unless otherwise specified.

Unless otherwise stated size separation of fragments in the examples below is carried out using standard techniques of agarose and polyacrylamide gel electrophoresis ("PAGE") as described in Sambrook and numerous other references such as Goeddel et al., *Nucleic Acids Res.*, 1980, 8: 4057.

Unless described otherwise, ligations are accomplished using standard buffers, incubation temperatures and times, approximately equimolar amounts of the DNA fragments to be ligated and approximately 10 units of T4 DNA ligase ("ligase") per 0.5 µg of DNA.

Example 1

Cloning of Human HLTEX11

The full length HLTEX11 gene which encodes a novel 7-transmembrane protein was isolated from a human spleen plasmid cDNA library using the GeneTrapper technology from Gibco BRL Life Technologies, Gaithersburg, MD. Partial EST sequence, derived from a cDNA library prepared from a human T-cell lymphoma, was first identified in an EST database to potentially code for a novel 7TM protein. From this EST sequence primers near the 5' end of the partial clone were designed for use with Gene Trapper methods to obtain the full length clone. Because Gene Trapper requires a plasmid cDNA library for screening (the existing T-cell lymphoma cDNA library is in phage), a 3'primer was made and used in conjunction with the 5' primers to screen nine different human tissue plasmid cDNA libraries commercially available from BRL by PCR, to see if this gene existed in any of these other libraries. Out of the nine cDNA libraries, only the spleen and the testis libraries contained our gene of interest with the spleen library exhibiting a much higher source of the gene than the testis library. Utilizing Gene Trapper, a number of positive clones were extracted from the spleen library. Two of the longer clones were sequenced and found to contain the complete gene. The sequence data from both clones were compiled to determine the DNA sequence shown in FIG. 1A. The longest open reading frame in the DNA sequence is predicted to encode a 339 amino acid protein as set forth in FIG. 1B. A Blast search of the protein sequence shows it has significant homology to other 7 transmembrane proteins. The highest homology identified was to a chicken G-protein-coupled receptor induced in activated T-cells and to a human platelet-activating factor receptor.

Example 2

Cloning and expression of Human HLTEX11 in a baculovirus expression system

The cDNA sequence encoding the full length human HLTEX11 protein, in the deposited clone is amplified using PCR oligonucleotide primers corresponding to the 5' and 3' sequences of the gene by known methods.

Once inserted into an expression vector, as described below, the 5' end of the amplified fragment encoding human HLTEX11 provides an efficient signal peptide. An efficient signal for initiation of translation in eukaryotic cells, as described by Kozak, M., *J Mol. Biol.*, 1987, 196: 947–950 is appropriately located in the vector portion of the construct.

The amplified fragment is isolated from a 1% agarose gel using a commercially available kit ("Geneclean," BIO 101 Inc., La Jolla, Calif.). The fragment then is digested with BamH1 and Asp718 and again is purified on a 1% agarose gel. This fragment is designated herein F2.

The vector pRG1 is used to express the HLTEX11 protein in the baculovirus expression system, using standard methods, such as those described in Summers et al, A MANUAL OF METHODS FOR BACULOVIRUS VECTORS AND INSECT CELL CULTURE PROCEDURES, Texas Agricultural Experimental Station Bulletin No. 1555 (1987). This expression vector contains the strong polyhedrin promoter of the *Autographa californica* nuclear polyhedrosis virus (AcMNPV) followed by convenient restriction sites. The signal peptide of AcMNPV gp67, including the N-terminal methionine, is located just upstream of a BamH1 site. The polyadenylation site of the simian virus 40 ("SV40") is used for efficient polyadenylation. For an easy selection of recombinant virus the beta-galactosidase gene from *E. coli* is inserted in the same orientation as the polyhedrin promoter and is followed by the polyadenylation signal of the polyhedrin gene. The polyhedrin sequences are flanked at both sides by viral sequences for cell-mediated homologous recombination with wild-type viral DNA to generate viable virus that express the cloned polynucleotide.

Many other baculovirus vectors could be used in place of pA2-GP, such as pAc373, pVL941 and pAcIM1 provided, as those of skill in the art will readily appreciate, that construction provides appropriately located signals for transcription, translation, trafficking and the like, such as an in-frame AUG and a signal peptide, as required The plasmid is digested with the restriction enzyme EcoR1 and then is dephosphorylated using calf intestinal phosphatase, using routine procedures known in the art. The DNA is then isolated from a 1% agarose gel using a commercially available kit ("Geneclean" BIO 101 Inc., La Jolla, Calif.). This vector DNA is designated herein "V2".

Fragment F2 and the dephosphorylated plasmid V2 are ligated together with T4 DNA ligase. *E. coli* HB101 cells are transformed with ligation mix and spread on culture plates. Bacteria are identified that contain the plasmid with the human HLTEX11 gene by digesting DNA from individual colonies using XbaI and BamHI and then analyzing the digestion product by gel electrophoresis. The sequence of the cloned fragment is confirmed by DNA sequencing. This plasmid is designated herein pBacG-Protein Coupled Receptor HLTEX11.

Five micrograms of the plasmid pBacG-Protein Coupled Receptor HLTEX11 is co-transfected with 1.0 µg of a commercially available linearized baculovirus DNA ("BaculoGold™ baculovirus DNA", Pharmingen, San Diego, Calif.), using the lipofectin method described by Felgner et al., *Proc. Natl Acad. Sci. USA*, 1987, 84: 7413–7417. One microgram of BaculoGold™ virus DNA and 5 µg of the plasmid pBacG-Protein Coupled Receptor HLTEX11 are mixed in a sterile well of a microtiter plate containing 50 µl of serum free Grace's medium (Life Technologies Inc., Gaithersburg, Md.). Afterwards 10 µl Lipofectin plus 90 µl Grace's medium are added, mixed and incubated for 15 minutes at room temperature. The transfection mixture is then added drop-wise to Sf9 insect cells (ATCC CRL 1711) seeded in a 35 mm tissue culture plate with 1 ml Grace's medium without serum. The plate is rocked back and forth to mix the newly added solution. The plate is then incubated for 5 hours at 27° C. After 5 hours the transfection solution is removed from the plate and 1 ml of Grace's insect medium supplemented with 10% fetal calf serum is added. The plate is put back into an incubator and cultivation is continued at 27° C. for four days.

After four days the supernatant is collected and a plaque assay is performed, as described by Summers and Smith, cited above. An agarose gel with "Blue Gal" (Life Technologies Inc., Gaithersburg) is used to allow easy identification and isolation of gal-expressing clones, which produce blue-stained plaques. (A detailed description of a "plaque assay" of this type can also be found in the user's guide for insect cell culture and baculovirology distributed by Life Technologies Inc., Gaithersburg, page 9–10).

Four days after serial dilution, the virus is added to the cells. After appropriate incubation, blue stained plaques are picked with the tip of an Eppendorf pipette. The agar containing the recombinant viruses is then resuspended in an Eppendorf tube containing 200 µl of Grace's medium. The agar is removed by a brief centrifugation and the supernatant containing the recombinant baculovirus is used to infect Sf9 cells seeded in 35 mm dishes. Four days later the supernatants of these culture dishes are harvested and then they are stored at 4° C. A clone containing properly inserted HLTEX11 is identified by DNA analysis including restriction mapping and sequencing. This is designated herein as V-HLTEX11.

Sf9 cells are grown in Grace's medium supplemented with 10% heat-inactivated FBS. The cells are infected with the recombinant baculovirus V-HLTEX11 at a multiplicity of infection ("MOI") of about 2 (about 1 to about 3). Six hours later the medium is removed and is replaced with SF900 II medium minus methionine and cysteine (available from Life Technologies Inc., Gaithersburg). Forty-two hours later, 5 µCi of $^{35}$S-methionine and 5 µCi $^{35}$S cysteine (available from Amersham, Arlington Heights, Ill.) are added. The cells are further incubated for 16 hours and then they are harvested by centrifugation, lysed and the labeled proteins are visualized by SDS-PAGE and autoradiography.

Example 3

Expression of HLTEX11 in COS cells

The expression plasmid, HLTEX11 HA, is made by cloning a cDNA encoding HLTEX11 into the expression vector pcDNAI/Amp (Invitrogen, Inc., Sand Diego, Calif.).

The expression vector pcDNAI/amp contains: (1) an *E. coli* origin of replication effective for propagation in *E. coli* and other prokaryotic cell; (2) an ampicillin resistance gene for selection of plasmid-containing prokaryotic cells; (3) an SV40 origin of replication for propagation in eukaryotic cells; (4) a CMV promoter, a polylinker, an SV40 intron, and a polyadenylation signal arranged so that a cDNA conveniently can be placed under expression control of the CMV promoter and operably linked to the SV40 intron and the polyadenylation signal by means of restriction sites in the polylinker.

A DNA fragment encoding the entire HLTEX11 precursor and a HA tag fused in frame to its 3' end is cloned into the polylinker region of the vector so that recombinant protein expression is directed by the CMV promoter. The HA tag corresponds to an epitope derived from the influenza hemagglutinin protein described by Wilson et al., *Cell*, 1984, 37:767. The fusion of the HA tag to the target protein allows easy detection of the recombinant protein with an antibody that recognizes the HA epitope.

The plasmid construction strategy is as follows.

The HLTEX11 cDNA of the deposit clone is amplified using primers that contained convenient restriction sites, much as described above regarding the construction of expression vectors for expression of HLTEX11 in *E. coli* and *S. fugiperda*.

To facilitate detection, purification and characterization of the expressed G-Protein Coupled Receptor HLTEX11, one of the primers contains a hemagglutinin tag ("HA tag") as described above.

Suitable primers can be for PCR amplification may be selected using known methods. Amplification of the insert may also be performed using known methods. The PCR amplified DNA fragment and the vector, pcDNAI/Amp, are digested with and then ligated. The ligation mixture is transformed into *E. coli* strain SURE (available from Stratagene, La Jolla, Calif. 92037). The transformed culture is plated on ampicillin media plates which then are incubated to allow growth of ampicillin resistant colonies. Plasmid DNA is isolated from resistant colonies and examined by restriction analysis and gel sizing for the presence of the HLTEX11-encoding fragment.

For expression of recombinant HLTEX11, COS cells are transfected with an expression vector, as described above, using DEAE-DEXTRAN, as described, for instance, in Sambrook et al.

Cells are incubated under conditions for expression of HLTEX11 by the vector.

Expression of the HLTEX11 HA fusion protein is detected by radiolabelling and immunoprecipitation, using methods described in, for example Harlow et al., ANTIBODIES: A LABORATORY MANUAL, 2nd Ed.; Cold Spring Harbor Laboratory Press, Cold Spring Harbor, N.Y. (1988). To this end, two days after transfection, the cells are labeled by incubation in media containing $^{35}$S-cysteine for 8 hours. The cells and the media are collected, and the cells are washed and the lysed with detergent-containing RIPA buffer: 150 mM NaCl, 0.1% SDS, 1% NP-40, 0.5% DOC, 50 mM TRIS, pH 7.5, as described by Wilson et al. cited above. Proteins are precipitated from the cell lysate and from the culture media using an HA-specific monoclonal antibody. The precipitated proteins are then analyzed by SDS-PAGE gels and autoradiography. An expression product of the expected size is seen in the cell lysate, which is not seen in negative controls.

Example 4
Gene therapeutic expression of Human HLTEX11

Fibroblasts are obtained from a subject by skin biopsy. The resulting tissue is placed in tissue-culture medium and separated into small pieces. Small chunks of the tissue are placed on a wet surface of a tissue culture flask, approximately ten pieces are placed in each flask. The flask is turned upside down, closed tight and left at room temperature overnight. After 24 hours at room temperature, the flask is inverted; the chunks of tissue remain fixed to the bottom of the flask; and fresh media is added (e.g., Ham's F12 media, with 10% FBS, penicillin and streptomycin). The tissue is then incubated at 37° C. for approximately one week. At this time, fresh media is added and subsequently changed every several days. After an additional two weeks in culture, a monolayer of fibroblasts emerges. The monolayer is trypsinized and scaled into larger flasks.

A vector for gene therapy is digested with restriction enzymes for cloning a fragment to be expressed. The digested vector is treated with calf intestinal phosphatase to prevent self-ligation. The dephosphorylated, linear vector is fractionated on an agarose gel and purified.

HLTEX11 cDNA capable of expressing active HLTEX11 is isolated. The ends of the fragment are modified, if necessary, for cloning into the vector. For instance, 5' overhanging may be treated with DNA polymerase to create blunt ends. 3' overhanging ends may be removed using S1 nuclease. Linkers may be ligated to blunt ends with T4 DNA ligase.

Equal quantities of the Moloney Murine Leukemia Virus linear backbone and HLTEX11 fragment are mixed together and joined using T4 DNA ligase. The ligation mixture is used to transform *E. Coli* and the bacteria are then plated onto agar-containing kanamycin. Kan$^r$ phenotype and restriction analysis confirm that the vector has the properly inserted gene.

Packaging cells are grown in tissue culture to confluent density in Dulbecco's Modified Eagles Medium (DMEM) with 10% calf serum (CS), penicillin and streptomycin. The vector containing the HLTEX11 gene is introduced into the packaging cells by standard techniques. Infectious viral particles containing the HLTEX11 gene are collected from the packaging cells, which now are called producer cells.

Fresh media is added to the producer cells, and after an appropriate incubation period media is harvested from the plates of confluent producer cells. The media, containing the infectious viral particles, is filtered through a MILLIPORE filter to remove detached producer cells. The filtered media then is used to infect fibroblast cells. Media is removed from a sub-confluent plate of fibroblasts and quickly replaced with the filtered media. POLYBRENE (Aldrich Chemical Co., Milwaukee, Wis.) may be included in the media to facilitate transduction. After appropriate incubation, the media is removed and replaced with fresh media. If the titer of virus is high, then virtually all fibroblasts will be infected and no selection is required. If the titer is low, then it is necessary to use a retroviral vector that has a selectable marker, such as neo or his, to select out transduced cells for expansion.

Engineered fibroblasts then may be injected into rats, either alone or after having been grown to confluence on microcarrier beads, such as CYTODEX 3 beads. The injected fibroblasts produce HLTEX11 product, and the biological actions of the protein are conveyed to the host.

Example 5
Transient expression of receptor in mammalian cell lines

In order to maximize receptor expression, 5' and 3' untranslated regions (UTRs) are removed from the receptor cDNA prior to insertion into a pCDN expression vector (Aiyar, N. et al., *Molecular and Cellular Biochemistry*, 1994, 131:75–86). Since PCR is used to trim the cDNA, the DNA sequences are routinely confirmed by routine sequencing methods prior to expression.

Initially transient transfection of HLTEX11 in COS cells is performed using the dextran sulfate method. In this method, $1 \times 10^7$ COS cells are grown in 245×245-mm tissue culture plates for 24 hours to 50–70% confluency. The cells are washed with PBS and then transfected with 100 µg of HLTEX11 cDNA in CMEM media containing 10% Neuserum 1% glutamine, DE dextran and chloroquine media and incubated for 3 hours. The cells are then shocked with 10% DMSO, washed and incubated for three days in DMEM medium containing 10% fetal bovine serum, 1% glutamine.

Example 6
Ligand binding studies with receptor

HLTEX11 is transiently expressed in COS cells as described above. Membranes are prepared and binding studies initiated using iodinated PAF. For positive controls, membranes are used from the CHO cells comprising a receptor known to be responsive to PAF.

Example 7
mRNA expression in Different Cell Types

Poly A⁺ RNA is isolated from various cell types using the well known guanidium thiocyanate acid-phenol method followed by isolation using oligo dT column. RNA dot blot analysis is performed with a template manifold apparatus (Scheicher & Schuell, Keene, N.H.) to assure uniform dot size. Poly A⁺ RNA is applied using 0.5 μg of RNA. The RNA samples are denatured by adjusting them to 1M formaldehyde and heating them to 55° C. for 15 minutes. The samples are diluted into 20 volumes of 3M NaCl containing 0.3M trisodium citrate and applied to nitrocellulose filters under a gentle vacuum. The filters are washed with additional diluted, baked at 80° C. for 2 hours and then hybridized under high stringency in 50% formamide, 5×SSPE, 5×Denhardt's reagent, 0.1% SDS, and 100 μg/ml yeast tRNA to a labeled probe produced from the HLTEX11. The blots are washed with 0.1×SSC, 0.1% SDS at 50° C. and exposed to X-ray film for 48 hours at −70° C. Quantitation of the dots is performed using Phospho-Imaging analysis and data in relative optical density units (OD Units) is determined.

---

What is claimed is:

1. An isolated polypeptide comprising an amino acid sequence having at least 15 contiguous amino acids from the amino acid sequence of SEQ ID NO: 2 wherein said polypeptide is free of other human proteins.

2. The polypeptide of claim 1 which comprises the amino acid sequence of SEQ ID NO: 2.

3. The isolated polypeptide of claim 1 comprising an amino acid sequence having at least 50 contiguous amino acids from the amino acid sequence of SEQ ID NO:2.

4. The isolated polypeptide of claim 1 comprising an amino acid sequence having at least 100 contiguous amino acids from the amino acid sequence of SEQ ID NO:2.

5. The isolated polypeptide of claim 1 comprising an amino acid sequence having at least 200 contiguous amino acids from the amino acid sequence of SEQ ID NO:2.

* * * * *